United States Patent
Diamond et al.

(10) Patent No.: US 10,654,787 B2
(45) Date of Patent: *May 19, 2020

(54) PREPARATION AND SEPARATION OF A DI-CARBOXYLIC ACID-CONTAINING MIXTURE

(71) Applicant: Archer-Daniels-Midland Company, Decatur, IL (US)

(72) Inventors: Gary M. Diamond, Menlo Park, CA (US); Eric L. Dias, Belmont, CA (US); Raymond Archer, San Jose, CA (US); Vincent J. Murphy, San Jose, CA (US); Thomas R. Boussie, Menlo Park, CA (US)

(73) Assignee: Archer-Daniels-Midland Company, Decatur, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/722,454

(22) Filed: Oct. 2, 2017

(65) Prior Publication Data
US 2018/0086688 A1    Mar. 29, 2018

Related U.S. Application Data

(63) Continuation of application No. 14/869,237, filed on Sep. 29, 2015, now Pat. No. 9,776,945.
(Continued)

(51) Int. Cl.
*C07C 51/47* (2006.01)
*C07C 51/23* (2006.01)
(Continued)

(52) U.S. Cl.
CPC .......... *C07C 51/47* (2013.01); *B01D 15/1821* (2013.01); *B01D 15/363* (2013.01);
(Continued)

(58) Field of Classification Search
None
See application file for complete search history.

(56) References Cited

U.S. PATENT DOCUMENTS 2,664,441 A    12/1953  Owens
2,985,589 A    5/1961   Broughton et al.
(Continued)

FOREIGN PATENT DOCUMENTS

EP    2345632 A1    7/2011
WO    0154790 A1    8/2001
(Continued)

OTHER PUBLICATIONS

Walaszek("D-Glucaric Acid Content of Various Fruits and Vegetables and Cholesterol-Lowering Effects of Dietary D-Glucarate in the Rat" Nutrition Research, 1996, No. 16, vol. 4, p. 673-681) (Year: 1996).*

(Continued)

*Primary Examiner* — Amy C Bonaparte
(74) *Attorney, Agent, or Firm* — Stinson LLP

(57) ABSTRACT

Processes for separating a di-carboxylic acid or salt thereof from a mixture containing the di-carboxylic acid or salt thereof and one or more other components are provided. Also separation media useful for these separation processes is provided. In particular, processes for preparing an aldaric acid are described, such as glucaric acid from glucose, which includes separating the aldaric acid from the reaction product. Also, various glucaric acid products are described.

24 Claims, 4 Drawing Sheets

Related U.S. Application Data

(60) Provisional application No. 62/057,084, filed on Sep. 29, 2014.

(51) Int. Cl.
*C07C 51/16* (2006.01)
*C07C 51/27* (2006.01)
*B01D 15/36* (2006.01)
*B01D 15/18* (2006.01)

(52) U.S. Cl.
CPC .............. *C07C 51/16* (2013.01); *C07C 51/23* (2013.01); *C07C 51/27* (2013.01)

(56) References Cited

U.S. PATENT DOCUMENTS

| | | | |
|---|---|---|---|
| 4,150,241 A | 4/1979 | Prescher et al. | |
| 4,332,623 A | 6/1982 | Ando et al. | |
| 4,379,751 A | 4/1983 | Yoritomi et al. | |
| 4,400,468 A | 8/1983 | Faber | |
| 4,620,034 A * | 10/1986 | Smits | C07H 7/027 562/525 |
| 4,970,002 A | 11/1990 | Ando et al. | |
| 5,068,418 A | 11/1991 | Kulprathipanja et al. | |
| 5,068,419 A | 11/1991 | Kulprathipanja et al. | |
| 5,127,957 A | 7/1992 | Heikkila et al. | |
| 5,132,456 A | 7/1992 | King et al. | |
| 5,198,120 A | 3/1993 | Masuda et al. | |
| 5,487,987 A | 1/1996 | Frost et al. | |
| 5,637,225 A | 6/1997 | Heikkila et al. | |
| 6,093,326 A | 7/2000 | Heikkila et al. | |
| 6,224,776 B1 | 5/2001 | Heikkila et al. | |
| 6,284,904 B1 | 9/2001 | Ponnampalam | |
| 7,390,408 B2 | 6/2008 | Kearney et al. | |
| 8,669,393 B2 | 3/2014 | Boussie et al. | |
| 8,669,397 B2 | 3/2014 | Boussie et al. | |
| 8,785,683 B2 | 7/2014 | Boussie et al. | |
| 9,216,937 B2 | 12/2015 | Archer | |
| 9,776,945 B2 * | 10/2017 | Diamond | B01D 15/1821 |
| 2009/0250653 A1 * | 10/2009 | Kiely | C04B 24/06 252/70 |
| 2010/0317822 A1 | 12/2010 | Boussie et al. | |
| 2010/0317823 A1 | 12/2010 | Boussie et al. | |
| 2011/0160483 A1 | 6/2011 | Rezkallah | |
| 2011/0306790 A1 | 12/2011 | Murphy et al. | |
| 2013/0158255 A1 | 6/2013 | Archer et al. | |
| 2013/0225785 A1 | 8/2013 | Dias et al. | |
| 2013/0310605 A1 | 11/2013 | Salem et al. | |
| 2013/0345473 A1 | 12/2013 | Archer et al. | |
| 2015/0152448 A1 * | 6/2015 | Ito | C12P 7/42 435/72 |
| 2015/0321187 A1 * | 11/2015 | Dias | B01J 37/0201 562/531 |

FOREIGN PATENT DOCUMENTS

| | | |
|---|---|---|
| WO | 2006041792 A2 | 4/2006 |
| WO | 2008019468 A1 | 2/2008 |

OTHER PUBLICATIONS

Ramachandran ("Gluconic Acid: Properties, Applications and Microbial Production" Food Technol. Biotechnol, 44(2), 2006, p. 185-195) (Year: 2006).*

Glucose ("Glucose" Merck Index entry, retrieved from https://www.rsc.org/Merck-Index/monograph/m5765/glucose?q=authorize on Jul. 10, 2018) (Year: 2018).*

Tartaric Acid ("L-Tartaric Acid" Merck Index entry, retrieved from https://www.rsc.org/Merck-Index/monograph/m10473/tartaric%20acid?q=authorize on Jul. 10, 2018) (Year: 2018).*

Hydroxypropanedioic acid ("Hydroxypropanedioic Acid" HMDB entry, retrieved from http://www.hmdb.ca/metabolites/HMDB0035227 on Jul. 10, 2018) (Year: 2018).*

Glucuronic acid ("Glucuronic acid", HMDB entry, retrieved from http://www.hmdb.ca/metabolites/HMDB0000127 on Jul. 10, 2018) (Year: 2018).*

Mopper ("Uronic and other organic acids in Baltic Sea and Black Sea sediments" Geochemica et Cosmochimica Acta, 1978, vol. 42, p. 153-163) (Year: 1978).*

ChemDraw appendix of composition components of Dirkx and their molecular weights, p. 1-5, created Jul. 2018 (Year: 2018).*

Smits ("Lead Modified Platinum on Carbon Catalysts for the Selective Oxidation of (2-)Hydroxycarbonic Acids, and Especially Polyhydroxycarbonic Acids to their 2-Keto Derivatives" Applied Catalysis, 33, 1987,p. 83-96) (Year: 1987).*

Besson ("Oxidation of glucose and gluconate on Pt, Pt Bi, and Pt Au catalysts" Recueil des Travaux Chimiques de Pays-Bas, 115/04, Apr. 1996, p. 217-221) (Year: 1996).*

Verhaar ("Ion-exchange chromatography of the main reaction products of the catalytic oxidation of d-glucose and d-gluconic acid" Carbohydrate Research, 73, 1979, p. 287-292) (Year: 1979).*

Ericsson, T., et al., "Anion-Exchange Chromatogrphy of Dicarboxylic Hydroxy Acids," 1977, J Chromatography, 134:337-342.

Jansen, L., et al., "Separation of Dicarboxylic Hydroxy Acids By Anion-Exchange Chromatography and Gas Chromatography," 1971, J Chromatography, 57:353-364.

Niu, W., et al., "Benzene-Free Synthesis of Adipic Acid," 2002, Biotechnol Prog, 18:201-211.

Rokushika, S., et al., "Anion Chromatography of Carboxylic Acids and Keto Acids Using a Hollow-Fibre Suppressor," 1982, J Chromatography, 253:87-94.

Tanaka, K., et al., "Separation of Carboxylic Acids on a Weakly Acidic Cation-Exchange Resin by Ion-Exclusion Chromatography," 1999, J Chromatography, 850:187-196.

John Bhatt Presentation, "Novasep Process: Advanced Purification Technologies for Bio-Based Chemicals," Frontiers Bio-Refining 2012, 24 pages.

Albright, R.L., Ph.D., ASI Presentation: "Architecture and Application of Porous Crosslinked Organic Polymers," 2011, Montreal, Canada, 48 pages.

Lee, H-J., et al., "Separation of Lactic Acid from Acetic Acid Using a Four-Zone SMB," 2004, Biotechnol Prog, 20:179-192.

Ruthven, D.M., et al., "Counter-Current and Simulated Counter-Current Adsorption Separation Processes," 1989, Chem Eng Sci, 44/5:1011-1038.

Santana, C.C., et al., "Adsorption in Simulated Moving Beds," Encyclopedia of Industrial Biotechnology: Bioprocess, Bioseparation, and Cell Technology, 2009, Edited by Michael C. Flickinger, 27 pages.

Basaran, T.Y., "Ion Exchangers in the Recovery of Tartaric Acid from Aqueous Solutions," Thesis submitted to The Graduate School of Natural and Applied Sciences of Middle East Technical University, Jul. 2006, 98 pages.

Industrial Organic Chemistry, "Chemicals and Polymers from Benzene, 7.2 Cyclohexane," 1996, 248-249.

Product Information Lewatit® MDS 4368, LANXESS Energizing Chemistry, Edition Oct. 13, 2011, 5 pages.

Nexant Thinking™ PERP Program, "Adipic Acid", PERP 2013-3, Dec. 2013, Nuno Faisca and Caleb Chong Wei Ping, 31 pages.

Davey, C-L., "Development of an Ion Chromatography Method for the Analysis of Nitric Acid Oxidation Reactions of Common Sugars," Master of Science Thesis submitted to The University of Waikato, 2008, 103 pages.

Brown, J.M., "Equilibration of D-Glucaric Acid in Aqueous Solution," Master of Science Thesis submitted to The University of Waikato, 2007, 191 pages.

Brown, J.M., et al., "An NMR Study of the Equilibration of D-Glucaric Acid with Lactone Forms in Aqueous Acid Solutions," 2007, J Carbohydrate Chem, 26:455-467.

Dirkx, J.M.H., et al., "The Preparation of D-Glucaric Acid by the Oxidation of D-Gluconic Acid Catalysed by Platinum on Carbon," 1977, Carbohydrate Res, 59:63-72.

Dirkx, J.M.H., et al., "The Oxidation of Glucose with Platinum on Carbon as Catalyst," 1981, J Catalysis, 67:1-13.

(56) References Cited

OTHER PUBLICATIONS

Smith, T.N., "Synthesis of Higher Molecular Weight Poly(D-glucaramides) and Poly(aldaramides) as Novel Gel Forming Agents," Ph.D. Chemistry Dissertation Presented to The University of Montanta, 2008, 169 pages.

Wu, J., et al., "Model-based Design of a Pilot-Scale Simulated Moving Bed for Purification of Citric Acid from Fermentation Broth" 2009, J Chromatogr A, 1216/50:8793-8805.

Venkateswarlu, G., et al., "Determination of Trace Impurities in Chromium Matrices After Separation from Cr(III) Using the Oxalate Form of Anion Exchanger," 2006, Talanta, 68/3:748-752, XP025001024.

International Search Report and Written Opinion issued in PCT/US2015/052981, dated Mar. 31, 2016, 19 pages.

Benkhäuser, C., "Improving Separations with Simulated Moving Bed Chromatography," Nov. 23, 2017, Insights from Industry, AZO Materials, https://www.azom.com/article.aspx?ArticleID=14824, downloaded Apr. 29, 2019, 10 pages.

\* cited by examiner

PREPARATION AND SEPARATION OF A DI-CARBOXYLIC ACID-CONTAINING MIXTURE

REFERENCE TO RELATED APPLICATIONS

This application is a continuation of U.S. patent application Ser. No. 14/869,237, filed Sep. 29, 2015, now U.S. Pat. No. 9,776,945, which claims priority to U.S. Provisional Application Ser. No. 62/057,084, filed Sep. 29, 2014, the entire disclosures of which are incorporated herein by reference.

FIELD OF THE INVENTION

The present invention generally relates to processes for separating a di-carboxylic acid or salt thereof from a mixture containing the di-carboxylic acid or salt thereof and one or more other components. The present invention also relates to separation media that are useful for these separation processes. Further, the present invention generally relates to processes for preparing an aldaric acid, such as glucaric acid from glucose, which includes separating the aldaric acid from the reaction product. Also, the present invention relates to various glucaric acid products.

BACKGROUND OF THE INVENTION

Processes for the preparation of di-carboxylic acids are known to produce crude mixtures containing various on-path and off-path carboxylic acids. Various waste streams from other processes may also contain di-carboxylic acids. Thus, separation of these mixtures and streams is necessary in order to obtain a sufficiently pure product or recover useful fractions of waste streams containing di-carboxylic acids. Methods for the separation and purification of carboxylic acids have been disclosed (See, for example, U.S. Pat. No. 6,284,904, U.S. Patent Application Publication No. 2013/0345473; J. Chromatogr. A. 850, 1999, p 187; J. Chromatogr. 57, 1971, p 353; J. Chromatogr. 253, 1982, p 87). Several of the methods disclosed in the art describe the use of anion exchange column chromatography with particular eluents such as organic acids (e.g., acetic acid or formic acid), bases (e.g., sodium bicarbonate or sodium tetraborate), and strong acids (e.g., sulfuric acid or hydrochloric acid).

Although industrial chromatographic separation methods are one approach for the separation of mono-carboxylic acids and di-carboxylic acids, the use of strong acids, organic acids, bases or eluent components other than water that may be necessary to produce an effective separation and elution is not desirable. These additional components increase reagent costs and may require disposal if recovery is not possible after use. Further, these additional components may necessitate additional equipment for removal and recovery after use, which increases process costs. Accordingly, there remains a need for an industrially advantageous separation process in which the eluent does not introduce extraneous components into process streams. Further, in processes for the production of di-carboxylic acids in which the reaction solvent is water, there remains a need for an industrially advantageous separation process in which water can be used as the primary eluent to facilitate the separation and elution of di-carboxylic acids from other components present in a crude reaction mixture.

Moreover, in processes for preparing di-carboxylic acids, such as in the oxidation of glucose to glucaric acid as described in U.S. Pat. No. 8,669,397 and oxidation of a pentose to pentaric acid (e.g., xylose to xylaric acid) as described in U.S. Pat. No. 8,785,683, which are incorporated herein by reference, there remains a need for efficient and cost effective separation techniques for the desired di-carboxylic acid to facilitate improved process yields and economics.

SUMMARY OF THE INVENTION

Briefly, the present invention includes processes for producing an extract comprising a di-carboxylic acid or salt thereof comprising: contacting a separation media in a separation zone with a feed mixture comprising the di-carboxylic acid or salt thereof and a second component, wherein at least a portion of the di-carboxylic acid or salt thereof is separated from the second component and a raffinate is formed comprising at least a portion of the second component; removing the raffinate from the separation zone; and eluting the di-carboxylic acid or salt thereof from the separation media with an eluent comprising water to form the extract comprising the di-carboxylic acid or salt thereof, wherein the extraneous acid concentration of the eluent, prior to contact with the separation media, is less than about 1 wt. %, less than about 0.5 wt. %, less than about 0.2 wt. %, less than about 0.1 wt. %, less than about 0.05 wt. %, or less than about 0.01 wt. %.

Further processes for producing an extract comprising a di-carboxylic acid or salt thereof comprise: contacting a separation media in a separation zone with a feed mixture comprising the di-carboxylic acid or salt thereof and a second component, wherein at least a portion of the di-carboxylic acid or salt thereof is separated from the second component and a raffinate is formed comprising at least a portion of the second component; removing the raffinate from the separation zone; and eluting the di-carboxylic acid or salt thereof from the separation media with an eluent to form the extract comprising the di-carboxylic acid or salt thereof, wherein the eluent is (i) makeup water and/or (ii) process water comprising water and optionally feed mixture constituents.

For example, various process for producing an extract comprising a di-carboxylic acid or salt thereof comprise: contacting a separation media in a separation zone with a feed mixture comprising the di-carboxylic acid or salt thereof and a second component, wherein at least a portion of the di-carboxylic acid or salt thereof and the second component are retained on the separation media; eluting at least a portion of the second component from the separation media with an eluent to form a raffinate comprising the second component; and removing the raffinate from the separation zone; eluting at least a portion of the di-carboxylic acid or salt thereof from the separation media with the eluent to form the extract comprising the di-carboxylic acid or salt thereof, removing the extract from the separation zone; wherein the weight ratio of the di-carboxylic acid or salt thereof to the second component in the extract is greater than the weight ratio of the di-carboxylic acid or salt thereof to the second component in the feed mixture and/or the raffinate. In various processes, the eluent comprises water and the extraneous acid concentration of the eluent, prior to contact with the separation media, is less than about 1 wt. %, less than about 0.5 wt. %, less than about 0.2 wt. %, less than about 0.1 wt. %, less than about 0.05 wt. %, or less than about 0.01 wt. %. In these and other processes, the eluent is (i) makeup water and/or (ii) process water comprising water and optionally feed mixture constituents.

Still further, other processes for producing an extract comprising a di-carboxylic acid or salt thereof of the present invention comprise: contacting a separation media in a separation zone with a feed mixture comprising the di-carboxylic acid or salt thereof and a second component, wherein at least a portion of the di-carboxylic acid or salt thereof is separated from the second component and a raffinate is formed comprising at least a portion of the second component; removing the raffinate from the separation zone; and eluting the di-carboxylic acid or salt thereof from the separation media with an eluent comprising water to form the extract comprising the di-carboxylic acid or salt thereof, wherein the separation media comprises a di-carboxylate form of an anion exchange chromatography resin.

For example, processes for producing an extract comprising a di-carboxylic acid or salt thereof comprise: contacting a separation media in a separation zone with a feed mixture comprising the di-carboxylic acid or salt thereof and a second component, wherein at least a portion of the di-carboxylic acid or salt thereof and the second component are retained on the separation media; eluting at least a portion of the second component from the separation media with an eluent comprising water to form a raffinate comprising the second component; and removing the raffinate from the separation zone; eluting at least a portion of the di-carboxylic acid or salt thereof from the separation media with the eluent comprising water to form the extract comprising the di-carboxylic acid or salt thereof, removing the extract from the separation zone; wherein the weight ratio of the di-carboxylic acid or salt thereof to the second component in the extract is greater than the weight ratio of the di-carboxylic acid or salt thereof to the second component in the feed mixture and/or the raffinate and wherein the separation media comprises a di-carboxylate form of an anion exchange chromatography resin.

The present invention also includes processes for preparing an aldaric acid, such as glucaric acid from glucose. The processes comprise: oxidizing an aldose with oxygen in the presence of an oxidation catalyst in an oxidation reaction zone to form an oxidation product comprising the aldaric acid and on-path intermediates to the aldaric acid; removing the oxidation product from the presence of the oxidation catalyst; and producing an extract comprising the aldaric acid according to any of the separation processes described herein, wherein the feed mixture comprises the aldaric acid as the di-carboxylic acid and on-path intermediates to the aldaric acid as the second component obtained from the oxidation product.

The present invention also includes various processes for preparing glucaric acid. Some of the processes comprise: reacting glucose with oxygen in the presence of an oxidation catalyst in an oxidation reaction zone to form an oxidation product comprising glucaric acid and on-path intermediates to glucaric acid; removing the oxidation product from the presence of the oxidation catalyst at a reaction endpoint wherein the molar yield of glucaric acid and lactones thereof at the reaction endpoint does not exceed about 30%, about 40%, about 45%, about 50%, or about 60% and the on-path percentage at the reaction endpoint, which is the sum of (a) the molar yields of glucaric acid, gluconic acid, guluronic acid, and glucuronic acid and (b) the percentage of unconverted glucose, is at least about 60%, at least about 70%, at least about 75%, or at least about 80%, at least about 85%, or at least about 90%; separating a glucaric acid product from on-path intermediates to glucaric acid obtained in the oxidation product; and recycling the on-path intermediates to the oxidation reaction zone.

Other processes of the present invention include, for example, a process for preparing adipic acid comprising reacting at least a portion of the glucaric acid and lactones thereof obtained in any of the oxidation processes described herein with hydrogen in the presence of a halogen-containing compound and a catalyst in a hydrodeoxygenation reaction zone to form adipic acid.

The present invention is further directed to various separation media, including separation media comprising an anion exchange chromatography resin in a di-carboxylate form.

The present invention is also directed to various glucaric acid products. One glucaric acid product comprises: from about 20 wt. % to about 65 wt. % glucaric acid, from about 25 wt. % to about 70 wt. % gluconic acid, less than about 10 wt. % of one or more ketogluconic acids, less than about 5 wt. % of one or more $C_2$-$C_5$ di-acids, and less than about 5 wt. % glucose, wherein each weight percent is based on the dissolved solids content of the glucaric acid product. Another glucaric acid product includes a concentrated glucaric acid product comprising from about 85 wt. % to about 99 wt. % glucaric acid, less than about 5 wt. % gluconic acid, less than about 2.5 wt. % of one or more ketogluconic acids, less than about 10 wt. % or one or more $C_2$-$C_5$ di-acids, and less than about 1 wt. % glucose, wherein each weight percent is based on the dissolved solids content of the concentrated glucaric acid product.

Other objects and features will be in part apparent and in part pointed out hereinafter.

DESCRIPTION OF THE PREFERRED EMBODIMENTS

Figure 1:
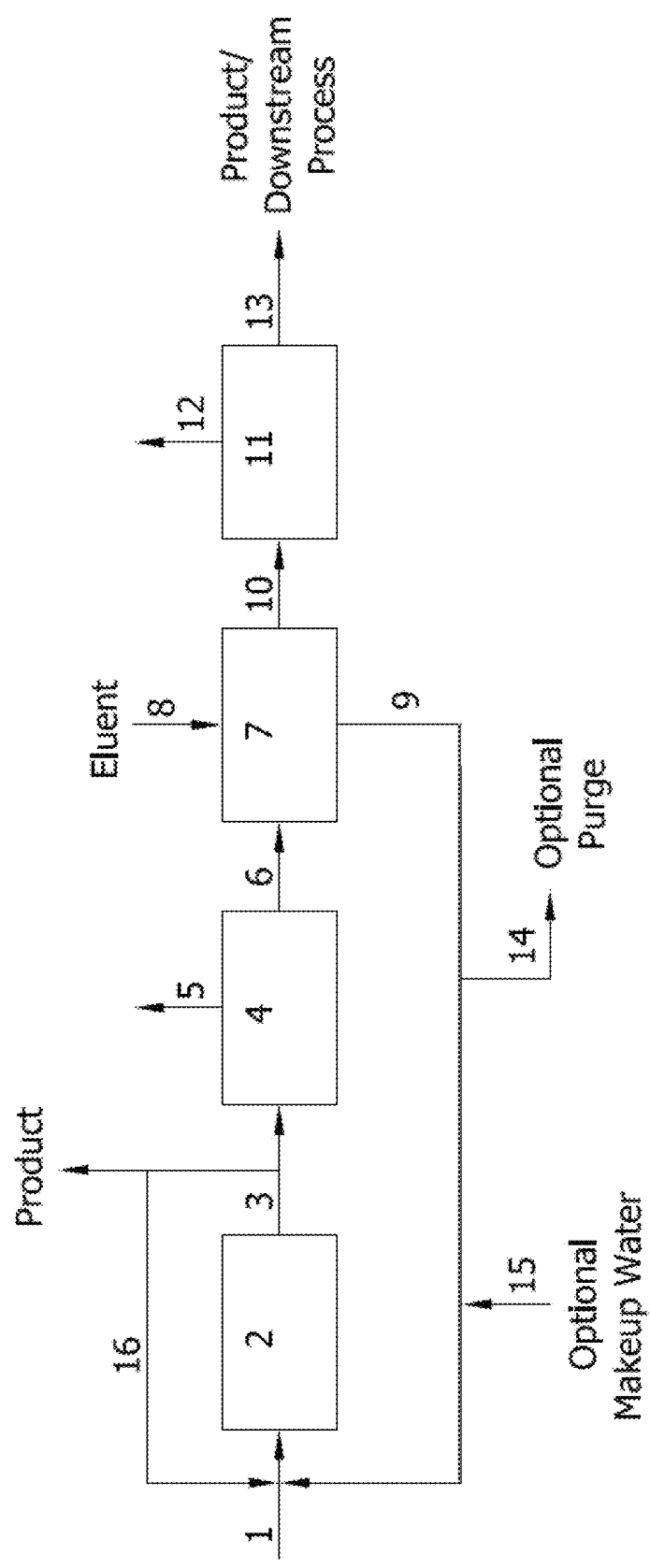
FIG. 1 depicts an example of a process flow diagram for an oxidation process including a separation process in accordance with the present invention. Other variations are possible.

Various aspects of the present invention relate to processes for separating a di-carboxylic acid from a mixture containing the di-carboxylic acid and one or more other components. Other aspects of the present invention relate to separation media that are useful for these separation processes. Further, aspects of the present invention relate to processes for preparing an aldaric acid, such as glucaric acid from glucose, which includes separating the aldaric acid from the reaction product. Also, various aspects of the present invention relate to processes for preparing an aldaric acid from an aldose, in which the processes have enhanced overall process yield. Further still, aspects of the present invention relate to various glucaric acid products.

As used herein, the terms "aldaric acid," "aldonic acid," and species thereof such as "glucaric acid" or "gluconic acid" or "xylaric acid" or "xylonic acid" each refer collectively to the acid and any corresponding lactones of that species that may be present. For example, in the presence of water, glucaric acid is known to be in equilibrium with glucaro-1,4-lactone, glucaro-6,3-lactone, and glucaro-1,4:6,3-dilactone. Therefore, unless specified otherwise, reference to "glucaric acid" is inclusive of these glucarolactone species as well. Also, although the following description refers to feed mixtures containing various mono-carboxylic acids and di-carboxylic acids, the separation processes of the present invention include those where at least a portion of these acids are in salt form, such as sodium, potassium, calcium, and magnesium salts (e.g., sodium glucarate), and the extract comprises a di-carboxylic acid or salt thereof.

One aspect of the present invention is directed to a chromatographic separation process for separating a di-carboxylic acid from a mixture containing the di-carboxylic acid and one or more other components wherein the eluent comprises water. A chromatographic separation process that uses water as eluent is advantageous because the introduction of extraneous acids or bases (e.g., sulfuric acid, hydrochloric acid, acetic acid, formic acid, sodium bicarbonate, sodium tetraborate, etc.) as eluents is reduced or avoided. A chromatographic separation process that uses water as eluent is especially beneficial in processes where water is the primary solvent because additional equipment for separation of the di-carboxylic acid from the eluent may not be required.

Another aspect of the present invention is directed to a chromatographic separation process for separating a di-carboxylic acid from a feed mixture containing the di-carboxylic acid and one or more other components wherein the separation media is highly selective for separating the di-carboxylic acid from other components in the feed. A highly efficient separation media and process for using this media advantageously provides an extract containing a greater portion of the desired di-carboxylic acid from the feed and a raffinate containing a greater portion of components from the feed that may be recycled.

Yet another aspect of the present invention is directed to an oxidation process for preparing aldaric acid from an aldose with enhanced overall process yield. Surprisingly, it has been found that a high overall aldaric acid process yield may be obtained when the oxidation reaction is controlled within certain endpoint limits and the di-carboxylic acid component of the oxidation product is efficiently separated from unreacted aldose and on-path intermediates, and thereby facilitating the recycle of the on-path intermediates to the oxidation reaction step.

In another aspect of the invention, separation processes of the present invention can also include a selective membrane separation (e.g., nano-filtration membranes) in combination with the chromatographic separation processes described herein. The selective membrane separation can be performed upstream and/or downstream of a chromatographic separation. For example, selective membrane separation techniques such as nano-filtration (NF) membrane separation can be used to reduce the amount of impurities contained in a mixture (e.g., a product mixture obtained from an oxidation process for preparing aldaric acid from an aldose) prior feeding the mixture to a chromatographic separation.

Also, another aspect of the present invention is directed to various integrated processes that include the separation process or separation media of the present invention.

Furthermore, another aspect of the present invention is directed to various separation media, including separation media comprising an anion exchange chromatography resin in the di-carboxylate form (e.g., a weak base anion exchange resin in glucarate form).

Further still, another aspect of the present invention is directed to various glucaric acid products prepared in accordance with various processes described herein.

Separation Processes and Media

The separation processes of the present invention include chromatographic separation processes using a separation media to produce an extract comprising a di-carboxylic acid. Typically, the processes comprise contacting a separation media in a separation zone with a feed mixture comprising the di-carboxylic acid and a second component wherein at least a portion of the di-carboxylic acid and the second component are retained on the separation media. The second component can comprise one constituent or a mixture of different constituents. Following contact of the separation media with the feed mixture, the process comprises eluting at least a portion of the second component from the separation media with an eluent to form a raffinate comprising the second component. In this step, at least a portion of the di-carboxylic acid is separated from the second component, and a raffinate is formed comprising at least a portion of the second component. The processes further include removing the raffinate from the separation zone and eluting at least a portion of the di-carboxylic acid from the separation media with the eluent to form the extract comprising the di-carboxylic acid. The eluent in these processes comprises water. The steps in the separation process may be conducted in any order and/or simultaneously. For example, feed mixture can be contacted with the separation media while raffinate is removed from the separation zone, and eluent can be added while raffinate and then extract are removed from the separation zone.

The separation processes of the present invention can also include an optional rinse step comprising rinsing the separation media, for example, with liquid such as eluent or other wash liquid to remove remaining feed constituents. After rinsing, the rinse liquid can be discharged from the separation zone.

Optionally, a closed loop recirculation step may be performed. During recirculation, the mobile phase is re-contacted with the separation media. Typically, feed mixture and eluent are not introduced to the separation zone and raffinate is not removed during recirculation of the extract.

Surprisingly, in various separation processes of the present invention, water has been found to be an effective eluent to elute the di-carboxylic acid from the separation media. Therefore, in separation processes in accordance with the present invention the eluent may comprise water. In various embodiments, the eluent comprising water contains little to no extraneous acid. In these and other embodiments, the eluent comprising water contains little to no extraneous base. "Extraneous acid" refers to acid that is added to the eluent. Similarly, "extraneous base" refers to base that is added to the eluent. Extraneous acid can also include acids that are not present in the separation feed mixture. Extraneous acids can include inorganic acids such as sulfuric acid and hydrochloric acid. Extraneous acids can also include organic acids such as acetic acid, formic acid, and oxalic acid. Oxalic acid may be present in the feed mixture of some processes. Thus, in some processes, the extraneous acid includes sulfuric acid, hydrochloric acid, acetic acid, and formic acid. Bases include, for example sodium hydroxide and potassium hydroxide.

Accordingly, one process for producing an extract comprising a di-carboxylic acid in accordance with the present invention comprises contacting a separation media in a separation zone with a feed mixture comprising the di-carboxylic acid and a second component, wherein at least a portion of the di-carboxylic acid is separated from the second component and a raffinate is formed comprising at least a portion of the second component; removing the raffinate from the separation zone; and eluting the dicarboxylic acid from the separation media with an eluent comprising water to form the extract comprising the di-carboxylic acid, wherein the extraneous acid concentration of the eluent, prior to contact with the separation media, is less than about 1 wt. %, less than about 0.9 wt. %, less than about 0.8 wt. %, less than about 0.7 wt. %, less than about 0.6 wt. %, less than about 0.5 wt. %, less than about 0.4 wt. %, less than about 0.3 wt. %, less than about 0.2 wt. %, less than about 0.1 wt. %, less than about 0.05 wt. %, or less than about 0.01 wt. %. In various embodiments, the eluent does not contain any extraneous acid (e.g., does not contain any measurable amount of extraneous acid). Further, in some embodiments, the eluent consists essentially of water or is water. In these various processes, when the separation media is contacted with the feed mixture, at least a portion of the di-carboxylic acid and the second component are retained on the separation media. Also, the raffinate comprising the second component is formed by eluting at least a portion of the second component from the separation media with the eluent. As a result of these separation processes, the weight ratio of the di-carboxylic acid to the second component in the extract is greater than the weight ratio of the di-carboxylic acid to the second component in the feed mixture and/or the raffinate.

In various separation processes of the present invention, the eluent is makeup water and/or process water. Makeup water can be, for example, deionized or distilled water. Process water is typically obtained from a process stage that generates water. For example, processes integrating a separation process of the present invention may include one or more stages for the concentration of various streams such as the extract, raffinate, or the feed mixture. In these stages, water may be removed from these process streams, for example, by flashing or evaporating to form process water. The process water removed from these streams may contain minor amounts of non-extraneous feed mixture components, such as mono- and di-carboxylic acids.

The eluent (e.g., water with little to no extraneous acid content, makeup water, and/or process water) can also be characterized by its pH. Accordingly, the pH of the eluent comprising water can be between about 5 and about 7.5, between about 5.5 and about 7.5, between about 6 and about 7.5, between about 6.5 and about 7.5, between about 5 and about 7, between about 5.5 and about 7, between about 6 and about 7, between about 6.5 and about 7, or approximately neutral.

Generally, the flow rate of the eluent to the separation zone is at least about 1, at least about 10, at least about 50, at least about 100, at least about 500, or at least about 1,000 kg/hr, or at least 10,000 kg/hr.

The feed mixture may optionally be degassed (or deoxygenated) using standard procedures to prevent or limit oxidative damage to the separation media and thereby extend the operational lifetime of the separation media. Standard procedures can include bubbling an inert gas such as nitrogen through the feed solution and can also include subjecting the feed to solution to a vacuum or low pressure protocol to facilitate degassing.

A wide variety of separation media can be used in the separation processes of the present invention (e.g., silicas, functionalized silicas, aluminas, carbons, functionalized and un-functionalized polystyrene, polyacrylamide, cross-linked polystyrenes, polyacrylates and other resins). For example, separation media comprising a basic chromatography media has been found to be particularly useful for the separation processes of the present invention. The basic chromatography media can comprise a basic chromatography resin. More particularly, the basic chromatography resin can comprise an anion exchange chromatography resin.

In various embodiments, the basic chromatography media comprises a weakly basic anion exchange chromatography resin. Weakly basic anion exchange chromatography resin can be further specified on the percentage of weak base and strong base functionality. Weak base functionality of an anion exchange chromatography resin is typically produced by activating the resin with a secondary amine, resulting in primary, secondary, or tertiary amine functional groups. On the other hand, strong base functionality of an anion exchange chromatography resin is typically produced by activating the resin with a tertiary amine, resulting in quaternary amine functional groups. Basic anion exchange chromatography resins can be bifunctional by including a mixture of weak base and strong base functionalities. U.S. Pat. Nos. 4,952,608; 4,988,738; 5,464,875; and 6,699,913, which are incorporated herein by reference, describe various processes for preparing basic anion exchange chromatography resins. Accordingly, in various embodiments, the basic chromatography media comprises from about 60% to about 100%, from about 60% to about 90%, from about 70% to about 90%, from about 70% to about 85%, from about 70% to about 80%, or from about 75% to about 80% weak base functionality. In these and other embodiments, the basic chromatography media comprises from about 0% to about 40%, from about 10% to about 25%, from about 0% to about 10%, from about 5% to about 40%, from about 5% to about 25%, from about 5% to about 10%, from about 10% to about 40%, from about 10% to about 35%, from about 15% to about 35%, from about 15% to about 30%, from about 20% to about 30%, or from about 20% to about 25% strong base functionality.

Applicants have discovered that a separation media comprising a di-carboxylate form of an anion exchange chromatography resin is especially suited for various separation processes of the present invention. Accordingly, the separation media comprising the di-carboxylate form of the anion exchange chromatography resin of the present invention can be used in various separation processes, including any of the separation processes described herein. Yet another process for producing an extract comprising a di-carboxylic acid in accordance with the present invention comprises contacting a separation media in a separation zone with a feed mixture comprising the di-carboxylic acid and a second component, wherein at least a portion of the di-carboxylic acid is separated from the second component and a raffinate is formed comprising at least a portion of the second component; removing the raffinate from the separation zone; and eluting the di-carboxylic acid from the separation media with an eluent comprising water to form the extract comprising the di-carboxylic acid, wherein the separation media comprises a di-carboxylate form of an anion exchange chromatography resin. As noted, when the separation media is contacted with the feed mixture, at least a portion of the di-carboxylic acid and the second component are retained on the separation media. Also, the raffinate comprising the second component is formed by eluting at least a portion of the second component from the separation media with the eluent. As a result of these separation processes, the weight ratio of the di-carboxylic acid to the second component in the extract is greater than the weight ratio of the di-carboxylic acid to the second component in the feed mixture and/or the raffinate.

Without being bound by theory, applicants believe that separation media comprising the di-carboxylate form of an anion exchange chromatography resin do not function primarily as conventional ion exchange resins where ions on the resin exchange with one or more components in the feed solution thereby reversibly binding the component to the exchange resin. Instead, the separation media of the present invention is believed to bind or attract the di-carboxylic acid primarily by chemical affinity. Although not essential, as a result of this functionality, water can be used more effectively as an eluent when using the separation media of the present invention.

The separation media in accordance with the present invention and for use in various separation processes described herein can comprise a $C_2$-$C_6$ di-carboxylate form of the anion exchange chromatography resin. In various embodiments, the di-carboxylate form of the anion exchange chromatography resin comprises an aldarate form of the anion exchange chromatography resin. In further embodiments, the di-carboxylate form of the anion exchange chromatography resin is selected from the group consisting of the oxalate, tartronate, malonate, tartrate, succinate, xylarate, arabinarate, ribarate, glutarate, glucarate, adipate, and mixtures thereof. One preferred form of the anion exchange chromatography resin includes the glucarate form. Another preferred form of the anion exchange chromatography resin includes the xylarate form. Yet another preferred form of the anion exchange chromatography resin includes the oxalate form.

The di-carboxylate form of the anion exchange chromatography resin can be prepared by conditioning the anion exchange chromatography resin with a di-carboxylic acid solution (i.e., flowing a di-carboxylic acid solution through a column containing the resin). For example, to prepare the glucarate form of the anion exchange chromatography resin, the anion exchange chromatography resin can be conditioned by flowing a solution of glucaric acid through the resin.

The di-carboxylic acid used to condition the anion exchange chromatography resin can comprise a di-carboxylic acid that is the same as an acid that is present in the feed mixture to the separation process. For example, in various separation processes of the present invention, the feed mixture comprises a di-carboxylic acid, which can include glucaric acid, and the separation media can comprise the glucarate form of an anion exchange chromatography resin.

Also, the di-carboxylic acid used to condition the anion exchange chromatography media can comprise a di-carboxylic acid that is present in the feed mixture to the separation process and is also the highest concentration di-carboxylic acid in the feed mixture. For example, in various separation processes of the present invention, the feed mixture comprises glucaric acid and if glucaric acid is the highest concentration di-carboxylic acid in the feed, then the separation media can comprise the glucarate form of an anion exchange chromatography resin.

Further, the di-carboxylic acid used to condition the anion exchange chromatography resin can comprise a di-carboxylic acid that is present in the feed mixture to the separation process and is also the di-carboxylic acid with the lowest pKa in the feed mixture. For example, in various separation processes of the present invention, the feed mixture comprises a mixture of di-carboxylic acids such as oxalic acid and glucaric acid and since oxalic acid has a pKa lower than glucaric acid, then the separation media can comprise the oxalate form of an anion exchange chromatography resin.

In various embodiments, the feed mixture can be used to condition the anion exchange chromatography resin. Using the feed mixture, which comprises the di-carboxylic acid selected as the conditioning acid, advantageously avoids costs associated with using a purified source of the di-carboxylic acid as the conditioning agent.

Conditioning of the anion exchange chromatography resin is preferably performed in a manner in which a high percentage (e.g., 90-100%) of the functional sites are conditioned to the di-carboxylate form. For example, in some circumstances, the pH of the conditioning solution may be adjusted (e.g., adjusted to a higher pH) to enhance the conditioning process such that a high percentage of the functional sites of the resin are converted to the di-carboxylate form. Conductivity and pH measurements can be used on the resin conditioning agent effluent to monitor the point at which the conditioning is completed.

The separation media as described herein can comprise a resin (e.g., a cross-linked polymer or copolymer of acrylonitrile, acrylic acid, or methacrylic acid). In various embodiments, the resin comprises a styrene-divinylbenzene (DVB) copolymer. In further embodiments, the resin comprises an acrylate-divinylbenzene (DVB) copolymer, methyl acrylate-divinylbenzene (DVB) copolymer, polyacrylonitrile polymer, polyacrylate polymer, or polymethacrylate polymer. For example, one preferred separation media in accordance with the present invention comprises an anion exchange chromatography resin in the di-carboxylate form wherein the resin comprises a styrene-divinylbenzene (DVB) copolymer.

The resin can be gel-type or macroporous resins. Gel-type resins are gel polymers that develop interchain porosity on swelling by a miscible liquid and have a pore size distribution having a significant fraction of micropores (i.e., pores having diameters less than 20 Å). In the polymerization process of gel-type resins, a cross-linker is more or less evenly distributed throughout the matrix. The pores are very small and their size is typically only a few Angstroms (Å), but the size is relatively constant. Hence, the gel-type resin matrix has a pseudo-crystalline structure. Macroporous resins are porous polymeric material with a non-collapsible, permanent pore structure in both the dry and solvated states and have a pore size distribution having a significant fraction of macropores (i.e., pores having diameters larger than 500 Å). Macroporous resins can be prepared using porogens or phase extenders to create artificial porosity in the tri-dimensional matrix. Once the polymerization reaction is finished, the porogen is removed from the matrix leaving voids in the polymer structure. In various embodiments, the separation media comprises a macroporous resin.

The separation processes of the present invention involve fractionating (i.e., separating) a di-carboxylic acid from a feed mixture comprising a di-carboxylic acid and a second component. Typically, the feed mixture comprises the di-carboxylic acid and the second component dissolved in water. Accordingly, the dissolved solids content of the feed mixture is generally at least about 20 wt. %, at least about 30 wt. %, at least about 40 wt. %, or at least about 50 wt. %, or at least about 60 wt. %. The dissolved solids content of the feed mixture can be from about 20 wt. % to about 70 wt. %, from about 20 wt. % to about 60 wt. %, from about 30 wt. % to about 70 wt. %, from about 30 wt. % to about 60 wt. %, from about 30 wt. % to about 50 wt. %, or from about 40 wt. % to about 60 wt. %. The di-carboxylic acid concentration in the feed mixture can comprise at least about 20 wt. %, at least about 30 wt. %, at least about 40 wt. %, or at least about 50 wt. % of the dissolved solids content. In various embodiments, the di-carboxylic acid concentration in the feed mixture is from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the dissolved solids content. Further, the second component concentration in the feed mixture is from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the dissolved solids content.

Generally, the separation processes of the present invention form an extract comprising at least a portion of the di-carboxylic acid. In these processes, the extract can comprise at least about 50 wt. %, at least about 60 wt. %, at least about 70 wt. %, at least about 80 wt. %, or at least about 90 wt. % of the di-carboxylic acid content of the feed mixture. In various embodiments, the extract comprises from about 55 wt. % to about 100 wt. %, from about 55 wt. % to 99 wt. %, from about 55 wt. % to about 95 wt. %, from about 55 wt. % to about 90 wt. %, from about 55 wt. % to about 85 wt. %, from about 55 wt. % to about 80 wt. %, from about 60 wt. % to about 90 wt. %, from about 60 wt. % to about 85 wt. %, from about 60 wt. % to about 80 wt. %, from about 70 wt. % to about 90 wt. %, from about 70 wt. % to about 85 wt. %, or from about 70 wt. % to about 80 wt. % of the di-carboxylic acid content of the feed mixture.

Generally, the separation processes also forms a raffinate comprising at least a portion of the second component. The raffinate can comprise at least about 60 wt. %, at least about 70 wt. %, at least about 80 wt. %, at least about 90 wt. %, or at least about 95 wt. % of the second component content of the feed mixture. In various embodiments, the raffinate comprises from about 60 wt. % to about 100 wt. %, from about 60 wt. % to about 95 wt. %, from about 60 wt. % to about 90 wt. %, from about 70 wt. % to about 100 wt. %, from about 70 wt. % to about 95 wt. %, from about 70 wt. % to about 90 wt. %, from about 80 wt. % to about 100 wt. %, from about 80 wt. % to about 95 wt. %, or from about 80 wt. % to about 90 wt. % of the second component content of the feed mixture.

The separation processes in accordance with the present invention are useful for separating a di-carboxylic acid (i.e., at least one di-carboxylic acid or a mixture of two or more di-carboxylic acids), and/or its corresponding salt from a feed mixture. The di-carboxylic acid can comprise a $C_2$ to $C_6$ di-carboxylic acid. Further, the di-carboxylic acid can comprise an aldaric acid, such as a $C_3$ to $C_6$ aldaric acid. In various embodiments, the di-carboxylic acid comprises one or more acids selected from the group consisting of oxalic acid, tartronic acid, malonic acid, tartaric acid, succinic acid, xylaric acid, arabinaric acid, ribaric acid, glutaric acid, glucaric acid, adipic acid and mixtures thereof.

In various embodiments, the di-carboxylic acid comprises a $C_6$ di-carboxylic acid. One preferred $C_6$ di-carboxylic acid comprises glucaric acid. In other embodiments, the di-carboxylic acid comprises a $C_5$ di-carboxylic acid. Preferred $C_5$ di-carboxylic acids include $C_5$ aldaric acids. In various embodiments, the $C_5$ aldaric acids acid comprises at least one acid selected from the group consisting of xylaric acid, ribaric acid, arabinaric acid, and mixtures thereof.

The second component of the feed mixture generally includes one or more constituents other than the di-carboxylic acid. For example, the second component can comprise a mono-carboxylic acid (i.e., at least one mono-carboxylic acid or a mixture of two or more mono-carboxylic acids). The mono-carboxylic acid can comprise a $C_1$ to $C_6$ mono-carboxylic acid. Further, the second component can comprise an aldonic acid, such as a $C_3$ to $C_6$ aldonic acid. In various embodiments, the second component comprises a mono-carboxylic acid selected from the group consisting of a $C_2$ mono-carboxylic acid, a $C_3$ mono-carboxylic acid, a $C_4$ mono-carboxylic acid, a $C_5$ mono-carboxylic acid, a $C_6$ mono-carboxylic acid, and mixtures thereof.

In various embodiments, the second component comprises a $C_6$ mono-carboxylic acid selected from the group consisting of gluconic acid, guluronic acid, glucuronic acid, and mixtures thereof. In further embodiments, the second component comprises a mixture comprising gluconic acid, guluronic acid, glucuronic acid, one or more ketogluconic acids. In other embodiments, the second component comprises at least one $C_5$ aldonic acid. In various embodiments, the $C_5$ aldonic acid comprises at least one acid selected from the group consisting of xylonic acid, ribonic acid, arabinonic acid, and mixtures thereof.

The second component can also comprise a sugar (alone or in combination with one or more mono-carboxylic acids). Typically, the sugar is selected from the group consisting of a pentose, hexose, and mixtures thereof. In various embodiments, the second component comprises glucose. In other embodiments, the second component comprises a pentose. In various embodiments, the pentose comprises at least one sugar selected from the group consisting of xylose, ribose, arabinose, and mixtures thereof.

Accordingly, the second component can comprise a mixture of the mono-carboxylic acids and sugars mentioned above.

Also, although the description herein refers to various mono-carboxylic acids and di-carboxylic acids, it should be noted that the processes of the present invention are also suitable for use in connection with the separation of such acids in circumstances where at least a portion of these acids are in salt form, such as sodium (e.g., sodium glucarate), potassium, calcium, magnesium, or other salt.

Further, the feed mixture, extract and/or raffinate can be essentially free of nitric acid and salts thereof. For example, the feed mixture, extract and/or raffinate can contain less that than about 0.1 wt. % or less than about 0.01 wt. % of nitric acid and salts thereof. The feed mixture, extract and/or raffinate can be free of nitric acid and salts thereof.

The separation processes of the present invention can be batch, semi-batch, or continuous. Advantageously, the separation processes of the present invention can be continuous separation processes. As a result, these separation processes can be integrated into existing continuous processes without significantly impacting production rates. In any of the separation processes disclosed herein the contacting the separation media with the feed mixture; eluting the second component from the separation media; removing the raffinate from the separation zone; and eluting the di-carboxylic acid from the separation media can be performed continuously.

In various separation processes of the present invention the separation zone can be a simulated moving bed (SMB) chromatography stage. Also, the separation zone can comprise a plurality of chromatography beds. The SMB stage can comprise sequential SMB (SSMB). Furthermore, the SMB chromatography stage comprises continuous SMB.

SMB is generally considered a continuous separation process that has many important industrial applications. In comparison to batch chromatography, SMB processes often have higher productivities, higher product purities and lower solvent consumption. See chapter 1 in Encyclopedia of Industrial Biotechnology: Bioprocesses, Bioseparation and Cell Technology: Wiley and Sons, 2009. SMB has been used in recovery and purification of several large-scale chemical products, including p-xylene, ethylbenzene, p-cresol, and p-cymene. SMB is employed at very large scale for separating glucose and fructose in the production of high fructose corn syrups using water alone as an eluent. See for example, Chem. Eng. Sci. 1989, 44, p 1011. SMB has also been used for the separation of carboxylic acids. See for example, Biotechnol. Prog. 2004, 20, p 179 and J. Chromatogr. A. 2009, 1216, p 8793.

In an SMB process, the use of multiple columns in a closed loop, coupled with coordinated valve switching between columns, enables the simulated movement of the stationary phase (separation media) in a counter-current direction to the movement of the mobile phase. A feed mixture containing two or more components to be separated is fed to the middle of the column configuration. The component that has the higher affinity for the solid phase travels in the direction of the simulated movement of the stationary phase while the component with the lower affinity for the stationary phase travels in the direction of the liquid-phase flow. This enables the separation and withdrawal of enriched fractions of the components as extract and raffinate streams.

The SMB can be continuous or sequential or comprise a combination of a continuous method and a sequential method. Sequential SMB can be considered a "continuous process" from an overall process stand point if operated under certain conditions. In a continuous SMB process, feed, eluent, raffinate, and extract streams typically flow continuously. In the sequential SMB process, some of the streams do not necessarily flow continuously. The sequential SMB process commonly comprises three basic phases: a feeding phase, an elution phase and a circulation phase. During the feeding phase, a feed solution and possibly also an eluent during a simultaneous eluting phase, is introduced into a predetermined column containing one or more packed beds, and simultaneously a product fraction or fractions are withdrawn. During the eluting phase, the eluent is introduced into a predetermined packed bed or predetermined packed beds, and during these phases two, three or even four product fractions are withdrawn. During the circulation phase the columns are connected into a loop, whereby no feed solution or eluent is supplied to the partial packed beds and no product fractions are withdrawn. However, circulation as such takes place during the three phases.

The continuous SMB process has been described, for example, in U.S. Pat. No. 2,985,589 (Universal Oil Prod. Co (UOP)). In this process the mixture to be fractionated is introduced into one partial packed bed and an eluent is introduced into another partial packed bed, and two product fractions are withdrawn substantially simultaneously. U.S. Pat. No. 5,198,120 (Japan Organo Co., Ltd.) describes a continuous SMB process in which the feed point is fixed. The feed is introduced sequentially once a cycle and simultaneously with the introduction of the feed a first extract fraction and raffinate are taken out from the system. The examples of this patent use a SMB consisting of eight packed columns linked with each other in series.

Sequential SMB (SSMB) processes are described in U.S. Pat. No. 4,332,623 (Mitsubishi Chemical Industries, Ltd.), U.S. Pat. No. 4,379,751 (Sanmatsu Kogyo Co., Ltd.) and U.S. Pat. No. 4,970,002 (Mitsubishi Kasei Technoengineers Ltd.), for instance. A sequential SMB process for the recovery of betaine and sucrose from beet molasses is described in U.S. Pat. No. 5,127,957 (Heikkila, H. et al.). SSMB is an enhanced version of the original SMB chromatography process, proposed early the 1980s by Yoritomi et al (U.S. Pat. No. 4,379,751). These SSMB processes are today the most efficient chromatographic processes for separation a feed stream into two product streams, the "extract" and the "raffinate" streams, and are used in a wide range of applications and industries (food, chemistry, antibiotics, and pharmaceuticals). While conventional SMB has only one step per column (six steps for a six column design), SSMB processes have at least two or three steps per column, which allows a better separation by increasing the injection and recovery accuracies.

To increase the separation capacity, yields and fraction purities and fraction dry substance concentrations, SMB modes including two or more loops or two or more separation profiles have been developed. In U.S. Pat. No. 6,093,326 (Danisco Finland Oy) and U.S. Pat. No. 5,637,225 (Xyrofin Oy), SMB processes including multiple loops are described. U.S. Pat. No. 6,224,776 (Cultor Corp.) discloses a method for fractionating a solution into two or more fractions in a SMB process where the separation system comprises at least two separation profiles in the same loop. Further, WO 2001/054790 A1 (also U.S. Pat. No. 7,390,408) (Amalgamated Res. Inc.) describes a column apparatus for a fluid processing system containing a shallow bed of material between fluid distribution plates of fractal design (Shallow Bed SMB and Fractal Fluid Distribution).

Important performance metrics for commercial scale SMB are 1) the productivity of the separation expressed in units of g (processed feed) per liter of stationary phase (resin) per day, and 2) the eluent (or water) to feed ratio which is defined as the ratio of the volume of eluent (or water) necessary to process one volume of feed material through the SMB unit for the desired separation. The productivity of the separation in g (processed feed) per liter of stationary phase material (resin) per day is directly related to a) the amount of the resin needed for the desired separation and b) the size and number of the SMB systems required at commercial scale. The productivity therefore has an inverse relationship with the cost of the SMB unit at scale and a high productivity is desirable for a lower cost separation. The water (or eluent) to feed ratio also impacts the cost of the separation and product purification as a higher water/eluent to feed ratio will increase the dilution of the product during the separation and necessitate a greater expense to evaporate the water for the isolation (or other further processing) of the product. It is therefore desirable to run the separation with a low water/eluent to feed ratio.

The present invention is directed to various separation processes which combine any one of the features described herein. For example, various processes for producing an extract comprising a di-carboxylic acid including a combination of features can comprise:

contacting a separation media in a separation zone with a feed mixture comprising the di-carboxylic acid and second component, wherein at least a portion of the di-carboxylic acid is separated from the second component and a raffinate is formed comprising at least a portion of the second component;

removing the raffinate from the separation zone; and eluting the di-carboxylic acid from the separation media with an eluent comprising water to form the extract comprising the di-carboxylic acid. The extraneous acid concentration of the eluent, prior to contact with the separation media, can be less than about 1 wt. %, less than about 0.5 wt. %, less than about 0.2 wt. %, less than about 0.1 wt. %, less than about 0.05 wt. %, or less than about 0.01 wt. % and/or the eluent is (i) makeup water and/or (ii) process water comprising water and optionally feed mixture constituents. Also, the separation media can comprise a di-carboxylate form of an anion exchange chromatography resin.

More particularly, various processes for producing an extract comprising a di-carboxylic acid including a combination of features can comprise:
  contacting a separation media in a separation zone with a feed mixture comprising the di-carboxylic acid and a second component wherein at least a portion of the di-carboxylic acid and the second component are retained on the separation media;
  eluting at least a portion of the second component from the separation media with an eluent to form a raffinate comprising the second component;
  removing the raffinate from the separation zone; and
  eluting the di-carboxylic acid from the separation media with the eluent to form the extract comprising the di-carboxylic acid, wherein the weight ratio of the di-carboxylic acid to the second component in the extract is greater than the weight ratio of the di-carboxylic acid to the second component in the feed mixture and/or the raffinate. The eluent comprises water and the extraneous acid concentration of the eluent, prior to contact with the separation media, can be less than about 1 wt. %, less than about 0.5 wt. %, less than about 0.2 wt. %, less than about 0.1 wt. %, less than about 0.05 wt. %, or less than about 0.01 wt. % and/or the eluent is (i) makeup water and/or (ii) process water comprising water and optionally feed mixture constituents. Also, the separation media can comprise a di-carboxylate form of an anion exchange chromatography resin.

Any of the features or modifications described above can be incorporated into this process. For example, contacting the separation media with the feed mixture; removing the raffinate from the separation zone; and eluting the di-carboxylic acid (e.g., glucaric acid) from the separation media can be performed continuously. Also, the separation zone can be a SMB chromatography stage. The separation zone can comprise a plurality of chromatography beds. Further, the SMB stage can comprise sequential SMB and/or continuous SMB chromatography.

The separation processes of the present invention can also include additional separation techniques. For example, it may be beneficial to remove certain impurity components from the feed mixture prior to the separation step. Certain impurity components that may preferentially bind to the separation media can impair the separation efficiency and potentially reduce the lifetime of the separation media. Components that can preferentially bind may include oligomers or polymers or other impurities such as color bodies. Such impurity components may be present at low concentrations in the feed mixture. Removal of such impurities can be accomplished by passing the feed mixture through a column containing an absorbent material such as polystyrene resin, ion exchange resin, and/or activated carbon. For example, exemplary ion exchange resins include anion exchange resins.

The separation processes of the present invention can also include a selective membrane separation (e.g., nano-filtration membranes) in combination with the chromatographic separation processes described herein. The selective membrane separation can be performed upstream and/or downstream of a chromatographic separation. For example, selective membrane separation techniques such as nano-filtration (NF) membrane separation can be used to reduce the amount of impurities contained in a mixture prior feeding to the chromatographic separation. In various embodiments, a NF membrane with a suitable Molecular Weight Cut Off (MWCO) can be used to separate lower molecular weight di-carboxylic acid such as one or more of $C_2$-$C_5$ di-carboxylic acids (including oxalic acid, tartronic acid, tartaric acid and/or trihydroxyglutaric acid) when present from higher molecular weight di-carboxylic acids such as $C_6$ di-carboxylic acids (e.g., glucaric acid). Specific examples of suitable NF membranes include, for example and without limitation, spiral wound NF membranes having a MWCO of 150-300 available from GE Water & Process Technologies, Inc. (DURACID KH-type, DL-type, HL-type, DK-type), Dow Water and Process Solutions (FilmTec Series), Koch Membrane Systems (SELRO series), Evonik Membrane Extraction Technologies (DURAMEM Series), and Borsig Membrane Technology GmbH (GMT-oNF Series). The NF membrane separation produces a permeate comprising one or more of the $C_2$-$C_5$ di-carboxylic acids and a retentate comprising a higher concentration of the higher molecular weight acids such as glucaric acid, gluconic acid, guluronic acid, glucuronic acid and ketogluconic acids.

Furthermore, the extract comprising the di-carboxylic acid obtained from a chromatographic separation process described herein can also contain $C_2$-$C_5$-diacids produced in the oxidation process. Accordingly, in various embodiments of the present invention include use of NF separation membranes to further purify the extract by separating lower in molecular weight di-carboxylic acids such as $C_2$-$C_5$ di-carboxylic acids higher molecular weight acids including di-carboxylic acids (e.g., glucaric acid). In these embodiments, the NF membrane separation produces a permeate comprising one or more of the $C_2$-$C_5$ di-carboxylic acids and a retentate comprising a higher concentration (and higher purity) of higher molecular weight acids including di-carboxylic acids. Additionally, since water can pass through to the permeate, the membrane separation will also concentrate the acids contained in the retentate. NF membrane separation techniques can be used to purify and concentrate the extract solution from a chromatographic separation process described herein.

Generally, a NF separation zone may comprise one or more NF membranes or modules and can be configured as either a single-pass or a multi-pass system. The membrane modules may be of various geometries and include flat (plate), tubular, capillary, or spiral wound membrane elements and the membranes may be of mono- or multilayer construction. The separation membranes and other components (e.g. support structure) of the membrane modules are preferably constructed to adequately withstand the conditions presented by the products to be purified. For example, the separation membranes are typically constructed of organic polymers such as cross-linked aromatic polyamides in the form of one or more thin film composites.

Membrane separation methods such as NF membrane separations are pressure-driven separation processes driven by the difference between the operating pressure and the osmotic pressure of the solution on the feed (or retentate) side of a membrane. The operating pressure within a membrane separation unit will vary depending upon the type of membrane employed, as osmotic pressure is dependent upon the level of transmission of solutes through the membrane. Operating pressures in the membrane separation unit are suitably achieved by passing the feed stream (e.g., incoming reaction constituents in the combination removed from the reaction zone or chromatographic separation system) through one or more pumps upstream of the membrane unit, for example, a combination booster pump and high-pressure pump arrangement. Generally, ultra-filtration operations exhibit lower osmotic pressures than NF operations, given the same feed solution. The driving force for transmission through the membrane (i.e., permeate flux) increases with the operating pressure. However, the benefits of increased operating pressure must be weighed against the increased energy (i.e., pumping) requirements and the detrimental effects (i.e., compaction) on membrane life.

Typically, the operating pressure utilized in the ultrafiltration operation is less than about 800 kPa absolute and preferably from about 200 to about 500 kPa absolute. Typically, the operating pressure utilized in the NF operation is less than about 1200 kPa absolute and preferably from about 600 to about 900 kPa absolute. High temperatures tend to decrease the useful life of selective membranes. Accordingly, the temperature of the aqueous combination introduced into the NF membrane separation unit is generally from about 20° C. to about 100° C., and from about 30° C. to about 60° C., or from about 30° C. to about 50° C. If necessary, the mixture fed to the membrane separation zone can be cooled prior to being introduced, for example, by indirect heat exchange with other process streams or with cooling water (e.g., as part of the quench step).

In order to maintain or enhance membrane separation efficiency and permeate flux, the membranes are periodically cleaned so as to remove contaminants from the surface of the membrane. Suitable cleaning includes cleaning-in-place (CIP) operations wherein the surface of the membrane is exposed to a cleaning solution while installed.

Oxidation Processes

Further aspects of the present invention are directed to various processes for preparing an aldaric acid by the selective oxidation of an aldose. Aldoses include, for example, pentoses and hexoses (i.e., C-5 and C-6 monosaccharides). Pentoses include ribose, arabinose, xylose, and lyxose, and hexoses include glucose, allose, altrose, mannose, gulose, idose, galactose, and talose. Generally, processes for the selective oxidation of an aldose to an aldaric acid comprise reacting the aldose with oxygen in the presence of an oxidation catalyst in an oxidation reaction zone to form an oxidation product comprising the aldaric acid. Processes for the selective oxidation of glucose to glucaric acid and pentose to pentaric acid (e.g., xylose to xylaric acid) are described in U.S. Pat. Nos. 8,669,397 and 8,785,683, respectively.

The selective oxidation of an aldose typically produces not only aldaric acid but various on-path intermediates to the aldaric acid. On-path intermediates include, for example, various aldonic acids, uronic acids and/or unreacted aldose, which upon further oxidation yield the aldaric acid. Recovery and recycle of these on-path intermediates increases the overall aldaric acid process yield and improves process economics. Accordingly, an oxidation process in accordance with the present invention comprises reacting an aldose with oxygen in the presence of an oxidation catalyst in an oxidation reaction zone to form an oxidation product comprising the aldaric acid and on-path intermediates to the aldaric acid; removing the oxidation product from the presence of the oxidation catalyst; and producing an extract comprising the aldaric acid according to any of the separation processes of the present invention described herein, wherein the feed mixture comprises the aldaric acid as the di-carboxylic acid and on-path intermediates to the aldaric acid as the second component obtained from the oxidation product.

For instance, one oxidation process in accordance with the present invention comprises reacting an aldose with oxygen in the presence of an oxidation catalyst in an oxidation reaction zone to form an oxidation product comprising the aldaric acid and on-path intermediates to the aldaric acid; removing the oxidation product from the presence of the oxidation catalyst; contacting a separation media in a separation zone with a feed mixture comprising the aldaric acid and on-path intermediates, wherein at least a portion of the aldaric acid is separated from the on-path intermediates and a raffinate is formed comprising at least a portion of the on-path intermediates; removing the raffinate from the separation zone; and eluting the aldaric acid from the separation media with an eluent comprising water to form the extract comprising the aldaric acid. When the separation media is contacted with the feed mixture, at least a portion of the aldaric acid and the on-path intermediates are retained on the separation media. Also, the raffinate comprising the on-path intermediates is formed by eluting at least a portion of the on-path intermediates from the separation media with the eluent. As a result, the weight ratio of the aldaric acid to the on-path intermediates in the extract is greater than the weight ratio of the aldaric acid to the on-path intermediates in the feed mixture and/or the raffinate.

FIG. 1 presents a process flow diagram for an oxidation process in accordance with the present invention. Oxidation reactor feed 1 comprising an aldose such as glucose is introduced into oxidation reaction zone 2. Oxidation product 3 exits the oxidation reaction zone 2 and can be collected as product, recycled and/or fed to optional concentration zone 4 where water 5 can be removed to concentrate the oxidation product. In various embodiments, the oxidation reactor zone can be operated with recycle loop 16 to enhance temperature control and mass transport. In this scenario the recycle flow and the flow of oxidation product 3 from zone 2 to optional zone 4 are both operated continuously. Product collection from the recycle loop enables the collection of useful glucaric acid products further described herein. Optional concentration zone 4 can include, for example, one or more evaporators and/or flash separators. The oxidation product 3 or concentrate thereof 6 (separation zone feed mixture) can then be fed to separation zone 7 (a chromatographic separation zone). In this zone, di-carboxylic acid (i.e., aldaric acid such as glucaric acid) is separated from a second component (e.g., comprising aldonic acid such as gluconic acid) of the separation zone feed mixture. The separation media in the separation zone is contacted with the feed mixture. Components of the feed mixture are retained on the separation media. Eluent is then introduced into the separation zone. Raffinate 9 comprising at least a portion of the second component is eluted and removed from the separation zone and optionally recycled to the oxidation reactor either directly or in combination with the aldose in feed 1. Eluent is also introduced to the separation zone to produce extract 10 comprising at least a portion of the di-carboxylic acid. A portion of raffinate 9 may optionally be purged (14) as needed to avoid accumulation of off-path intermediates. Fresh makeup water 15 may be added to raffinate 9 that is recycled. Alternatively, the raffinate can be introduced to a concentration zone (not shown) to remove water before recycling to the oxidation reactor.

Extract 10 is removed from separation zone 7 and can be introduced into optional concentration zone 11 to further concentrate the extract. Extract 10 or concentrated extract 13 can be removed from the process as products or sent to downstream processes for further conversion. Process water 5, process water 12 or fractions thereof that are removed from optional concentration zones 4 and 11 (and optionally from the raffinate stream 9) can be recycled for use as eluent 8. Multiple variations of the process scheme shown in FIG. 1 are possible.

Any features described herein with respect to the separation process can be used either singularly or in combination in conjunction with the separation of a di-carboxylic acid from the oxidation product produced as described herein. For example, the extraneous acid concentration of the eluent, prior to contact with the separation media, can be less than about 1 wt. %, less than about 0.5 wt. %, less than about 0.2 wt. %, less than about 0.1 wt. %, less than about 0.05 wt. %, or less than about 0.01 wt. %. Further, the eluent can be (i) makeup water and/or (ii) process water comprising water and optionally feed mixture constituents. Also, the separation media can comprise a di-carboxylate form of an anion exchange chromatography resin.

As noted above, in various embodiments, the aldose is glucose. Glucose may be converted to glucaric acid by reacting glucose with oxygen (e.g., air, oxygen-enriched air, oxygen alone, or oxygen with other constituents substantially inert to the reaction) in the presence of an oxidation catalyst according to the following reaction:

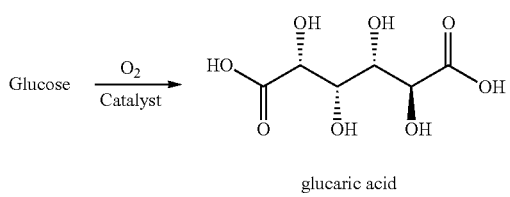 [SMILES: "O2" ; O=C(O)[C@@H](O)[C@@H](O)[C@H](O)[C@@H](O)C(=O)O]

glucaric acid

The oxidation can be conducted in the absence of added base (e.g., KOH) or where the initial pH of the reaction medium and/or the pH of reaction medium at any point in the reaction is no greater than about 7, no greater than 7.0, no greater than about 6.5, or no greater than about 6. The initial pH of the reaction mixture is the pH of the reaction mixture prior to contact with oxygen in the presence of an oxidation catalyst. In fact, catalytic selectivity can be maintained to attain glucaric acid yield in excess of about 30%, about 40%, about 50%, about 60% and, in some instances, attain yields in excess of 65% or higher. The absence of added base advantageously facilitates separation and isolation of the glucaric acid, thereby providing a process that is more amenable to industrial application, and improves overall process economics by eliminating a reaction constituent. The "absence of added base" as used herein means that base, if present (for example, as a constituent of a feedstock), is present in a concentration which has essentially no effect on the efficacy of the reaction; i.e., the oxidation reaction is being conducted essentially free of added base.

The oxidation reaction may be conducted under increased oxygen partial pressures and/or higher oxidation reaction mixture temperatures, which tends to increase the yield of glucaric acid when the reaction is conducted in the absence of added base or at a pH below about 7. Typically, the partial pressure of oxygen is at least about 15 pounds per square inch absolute (psia) (104 kPa), at least about 25 psia (172 kPa), at least about 40 psia (276 kPa), or at least about 60 psia (414 kPa). The partial pressure of oxygen can be up to about 1,000 psia (6895 kPa), more typically in the range of from about 15 psia (104 kPa) to about 500 psia (3447 kPa), from about 40 psia (276 kPa) to about 250 psia (1724 kPa), from about 75 psia (517 kPa) to about 500 psia (3447 kPa), from about 100 psia (689 kPa) to about 500 psia (3447 kPa), from about 150 psia (1034 kPa) to about 500 psia (3447 kPa). Generally, the temperature of the oxidation reaction mixture is at least about 40° C., at least about 60° C., at least about 70° C., at least about 80° C., at least about 90° C., at least about 100° C., at least about 110° C., at least about 120° C., or higher. The temperature of the oxidation reaction mixture can be from about 40° C. to about 200° C., from about 60° C. to about 200° C., from about 70° C. to about 200° C., from about 80° C. to about 200° C., from about 80° C. to about 180° C., from about 80° C. to about 150° C., from about 90° C. to about 180° C., or from about 90° C. to about 150° C.

Oxidation of glucose to glucaric acid can also be conducted in the absence of nitrogen as an active reaction constituent. Some processes employ nitrogen compounds such as nitric acid as an oxidant. The use of nitrogen in a form in which it is an active reaction constituent, such as nitrate or nitric acid, results in the need for $NO_x$ abatement technology and acid regeneration technology, both of which add significant cost to the production of glucaric acid from these known processes, as well as providing a corrosive environment which may deleteriously affect the equipment used to carry out the process. By contrast, for example, in the event air or oxygen-enriched air is used in the oxidation reaction of the present invention as the source of oxygen, the nitrogen is essentially an inactive or inert constituent. An oxidation reaction employing air or oxygen-enriched air is a reaction conducted essentially free of nitrogen in a form in which it would be an active reaction constituent. Thus, in various embodiments, the oxidation reaction mixture (i.e., glucaric acid product and process streams obtained therefrom, including the feed mixture to the chromatographic separation process as described herein, the resulting extract and/or raffinate can be free or essentially free of nitric acid and salts thereof. For example, these process streams can contain less that than about 0.1 wt. % or less than about 0.01 wt. % of nitric acid and salts thereof.

Generally, the oxidation catalyst comprises at least one d-block metal as the catalytically active component. More typically, the oxidation comprises at least one metal selected from the group consisting of platinum, palladium, and a combination thereof. Preferred oxidation catalysts comprise at least platinum as a catalytically active component. The oxidation catalyst can comprise a second metal. One preferred second metal includes gold. Oxidation catalysts are described in U.S. Patent Application Publication 2011/0306790, which is incorporated herein by reference. This publication describes various oxidation catalysts comprising platinum and gold, which are useful for the selective oxidation of compositions comprised of a primary alcohol group and at least one secondary alcohol group (e.g., glucose). Thus, one preferred oxidation catalyst comprises at least platinum and gold as the catalytically active component.

The oxidation catalyst is preferably a heterogeneous catalyst. Catalyst supports for the heterogeneous catalyst include zirconias, titania, or carbon (especially porous carbon black supports) as described in PCT/US2015/028358. The supports can be shaped supports such as extrudates, spheres, beads, cylinders, pellets, multi-lobed shapes, rings, stars, wheels, etc. Preferred shaped supports include extruded cylinders or extruded multi-lobed shapes such as trilobes. Accordingly, one oxidation catalyst comprises platinum and gold on a porous carbon black support. The platinum and gold can optionally be in a shell layer at or near external surfaces of the shaped porous carbon black support. For example, one oxidation catalyst contains platinum and gold in a shell wherein the shell thickness is from about 10 μm to 400 μm.

The oxidation of glucose to glucaric acid may be conducted in various known industrial reactor formats such as batch slurry, continuous slurry based stirred tanks or loop reactors, fixed bed, ebulated bed, bubble column, etc. A preferred reactor is a continuous flow fixed bed reactor. The oxidation reaction zone can comprise one or more reactors.

The oxidation of glucose to glucaric acid proceeds according to a multi-step reaction pathway as shown below. The reaction can proceed through the selective oxidation of the C-1 and C-6 carbon atoms in either order. For a selective reaction, the C-6 primary alcohol must be oxidized preferentially over the C-2 to C-5 secondary alcohol groups.

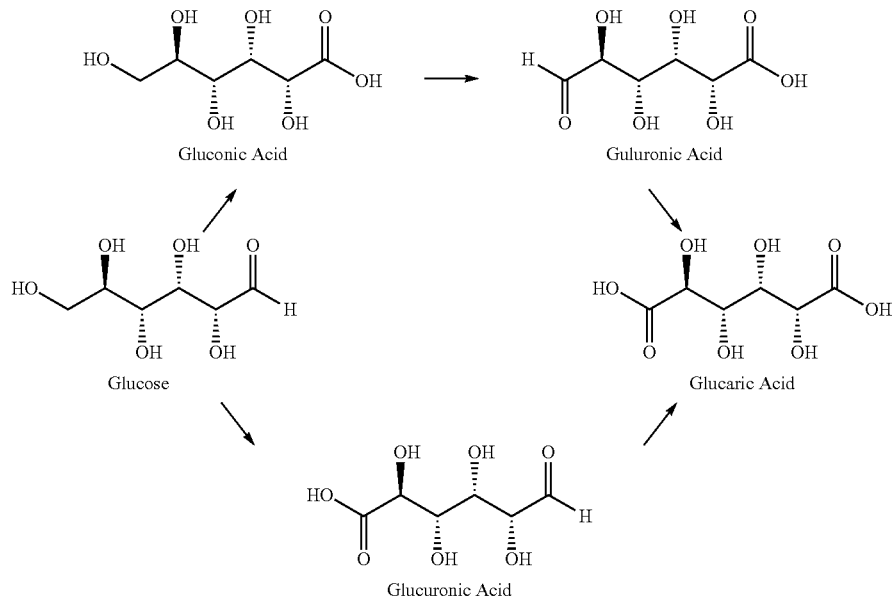

Thus, as shown in the scheme above, the principal on-path intermediates present in the selective oxidation of glucose are mono-carboxylic acids: gluconic acid, guluronic acid, and glucuronic acid.

In many processes for the direct catalytic oxidation of glucose to glucaric acid, molar glucaric acid yields are limited to about 65% and below. One of the reasons for the yield limitation is associated with the fact that glucaric acid can be further oxidized under the reaction conditions, and consequently as the concentration of glucaric acid increases in the reaction mixture, the oxidation of glucaric acid takes place which typically yields shorter chain, lower carbon number di-carboxylic acids (for example, di-carboxylic acid with 5 carbon atoms (e.g. xylaric acid), 4 carbon atoms (e.g. tartaric acid), 3 carbon atoms (e.g. tartronic acid), and 2 carbon atoms (e.g. oxalic acid)). Additionally, the production of other side-products is also known to lower the yield of glucaric acid. Ketogluconic acids can be produced from the oxidation of the secondary alcohol groups of the intermediate gluconic acid. Ketogluconic acids can also be oxidized to shorter chain di-acids and thereby reduce the yield of glucaric acid. Consequently, multiple competing reactions can reduce the selectivity for the oxidation of glucose to glucaric acid resulting in lower yields than desirable A direct consequence of the presence of high quantities of on-path intermediates such as gluconic acid and guluronic acid and off-path intermediates such as ketogluconic acids and numerous other di-carboxylic acids, is a difficult and costly purification of glucaric acid from a complex reaction product mixture. However, applicants have discovered that the separation processes of the present invention are especially suited for separating glucaric acid from a complex oxidation reaction mixture. Accordingly, another oxidation process in accordance with the present invention comprises reacting glucose with oxygen in the presence of an oxidation catalyst in an oxidation reaction zone to form an oxidation product comprising glucaric acid and on-path intermediates to glucaric acid; removing the oxidation product from the presence of the oxidation catalyst; and producing an extract comprising glucaric acid according to any of the separation processes of the present invention described herein, wherein the feed mixture to the separation process comprises glucaric acid as the di-carboxylic acid and on-path intermediates to glucaric acid as the second component obtained from the oxidation product. Unreacted glucose can also be separated from glucaric acid with the on-path intermediates.

Another oxidation process in accordance with the present invention comprises reacting glucose with oxygen in the presence of an oxidation catalyst in an oxidation reaction zone to form an oxidation product comprising glucaric acid and on-path intermediates to glucaric acid; removing the oxidation product from the presence of the oxidation catalyst; contacting a separation media in a separation zone with a feed mixture comprising glucaric and on-path intermediates, wherein at least a portion of glucaric acid is separated from the on-path intermediates and a raffinate is formed comprising at least a portion of the on-path intermediates; removing the raffinate from the separation zone; and eluting glucaric acid from the separation media with an eluent comprising water to form the extract comprising glucaric acid. When the separation media is contacted with the feed mixture, at least a portion of the glucaric acid and the on-path intermediates are retained on the separation media. Also, the raffinate comprising the on-path intermediates is formed by eluting at least a portion of the on-path intermediates from the separation media with the eluent. As a result of these separation processes, the weight ratio of the glucaric acid to the on-path intermediates in the extract is greater than the weight ratio of the glucaric acid to the on-path intermediates in the feed mixture and/or the raffinate.

It has been found that a high overall glucaric acid process yield may be obtained when the oxidation reaction is controlled within certain endpoint limits, the di-carboxylic acid component of the oxidation product is separated from on-path intermediates, and the on-path intermediates are recycled back to the oxidation reaction. The process discovered by applicants reduces the concentration of off-path intermediates such as $C_2$-$C_5$ di-acids while providing relatively high yields of glucaric acid under the oxidation reaction conditions. This process for preparing glucaric acid in accordance with the present invention generally comprises reacting glucose with oxygen in the presence of an oxidation catalyst in an oxidation reaction zone to form an oxidation product comprising glucaric acid and on-path intermediates to glucaric acid; removing the oxidation product from the presence of the oxidation catalyst at a reaction endpoint; separating a glucaric acid product from on-path intermediates to glucaric acid obtained in the oxidation product; and; and recycling the on-path intermediates to the oxidation reaction zone. In this process, the glucaric acid product can be an extract prepared according to any of the separation processes of the present invention described herein, wherein the feed mixture to the separation process comprises glucaric acid as the di-carboxylic acid and the second component comprises the on-path intermediates to glucaric acid obtained from the oxidation product.

In oxidation processes of the present invention, the reaction endpoint can be established according to a certain maximum molar yield of glucaric acid and lactones thereof (collectively referred to as glucaric acid yield). As noted, lactones of glucaric acid generally include glucaro-1,4-lactone, glucaro-1,4:3,6-dilactone, and glucaro-3,6-lactone. Applicants have found that if the molar glucaric acid yield is controlled within a certain range, then the concentration of less desirable shorter chain, lower carbon number di-carboxylic acid by-products is reduced and the majority of the constituents of the reaction mixture are glucaric acid plus on-path intermediates to glucaric acid (i.e., gluconic acid, guluronic acid, and glucuronic acid). More particularly, the oxidation product can be removed from the presence of the oxidation catalyst at a reaction endpoint wherein the molar yield of glucaric acid and lactones thereof at the reaction endpoint does not exceed about 30%, about 40%, about 45%, about 50%, or about 60%. In various embodiments, the oxidation product can be removed from the presence of the oxidation catalyst at a reaction endpoint wherein the molar yield of glucaric acid and lactones thereof at the reaction endpoint is from about 30% to about 65%, from about 30% to about 60%, from about 30% to about 50%, from about 40% to about 65%, from about 40% to about 60%, from about 50% to about 65%, or from about 50% to about 60%

Another important metric for a high overall process yield for glucaric acid is the "on-path percentage" for glucaric acid which includes unconverted glucose in the reactor exit, on-path intermediates to glucaric acid, and glucaric acid. For the purposes of establishing a reaction endpoint (based on on-path percentage), the on-path percentage is calculated according to equation (A):

$$\text{On path percentage} = \sum \begin{pmatrix} \text{molar yield of glucaric acid} + \\ \% \text{ of unconverted glucose} + \\ \text{molar yield of on path intermediates} \end{pmatrix} \quad (A)$$

where the on-path intermediates are (i) gluconic acid, (ii) guluronic acid, and (iii) glucuronic acid. Unless otherwise stated, "yields" of the reaction constituents referred to herein are calculated according to equation (B):

$$\frac{\text{moles of reaction constituent}}{\text{moles of glucose in oxidation reactor feed}} \times 100\% \quad (B)$$

Accordingly, the oxidation product can be removed from the presence of the oxidation catalyst at a reaction endpoint wherein the on-path percentage (according to equation (A)) at the reaction endpoint is at least about 60%, at least about 70%, at least about 75%, or at least about 80%, at least about 85%, or at least about 90%. In various embodiments, the oxidation product can be removed from the presence of the oxidation catalyst at a reaction endpoint wherein the on-path percentage at the reaction endpoint is from about 60% to about 100%, from about 65% to about 100%, from about 70% to about 100%, from about 60% to about 99%, from about 65% to about 99%, from about 70% to about 99%, from about 60% to about 95%, from about 65% to about 95%, or from about 70% to about 95%.

In various processes according to the present invention, a combination of the molar yield of glucaric acid and lactones thereof and the on-path percentage can be used as an important metric to help maximize overall process yield of glucaric acid. Accordingly, another process of the present invention for preparing glucaric acid comprises reacting glucose with oxygen in the presence of an oxidation catalyst in an oxidation reaction zone to form an oxidation product comprising glucaric acid and on-path intermediates to glucaric acid; removing the oxidation product from the presence of the oxidation catalyst at a reaction endpoint wherein the molar yield of glucaric acid and lactones thereof at the reaction endpoint does not exceed about 30%, about 40%, about 45%, about 50%, or about 60% and the on-path percentage at the reaction endpoint is at least about 60%, at least about 70%, at least about 75%, or at least about 80%, or at least about 85%, or at least about 90%, producing an extract comprising glucaric acid, wherein the feed mixture comprises glucaric acid as the di-carboxylic acid and on-path intermediates to glucaric acid as the second component obtained from the oxidation product; and recycling the on-path intermediates to the oxidation reaction zone.

In certain instances, applicants have found that if the molar glucaric acid yield is limited, then the on-path percentage is high. In particular, when the molar glucaric acid yield is limited to less than about 60%, then the on-path percentage is at least about 75%. In some instances, when the molar glucaric acid yield is limited to less than about 60%, then the on-path percentage is at least about 80%. In other instances, when the molar glucaric acid yield is limited to less than about 50%, then the on-path percentage is at least about 85%, or in some embodiments at least about 90%.

Applicants have found that a process to convert glucose to glucaric acid in which the oxidation reaction is run to lower molar yields with high on-path percentage coupled with an efficient separation of glucaric acid and recycle of glucose and the reaction intermediates enables a glucaric acid process yield at least about 75%, at least about 80%, at least about 85%, or at least about 90%, where yield is calculated according to equation B.

The manner in which the molar yield of glucaric acid is limited (i.e., to prevent further oxidation at the reaction endpoint) can be carried out in various known industrial reactors. For example, a continuous flow fixed bed reactor containing the oxidation catalyst composition can be run in a manner to limit the molar yield of glucaric acid by choosing an appropriate temperature, oxygen partial pressure, oxygen to glucose molar ratio and residence time in the fixed bed reactor.

The present invention is directed to various oxidation processes which combine any one of the features described herein. For example, one process featuring a combination of features is a process for preparing glucaric acid. This process comprises reacting glucose with oxygen in the presence of an oxidation catalyst in an oxidation reaction zone to form an oxidation product comprising glucaric acid and on-path intermediates to glucaric acid;

removing the oxidation product from the presence of the oxidation catalyst at a reaction endpoint wherein the molar yield of glucaric acid and lactones thereof at the reaction endpoint does not exceed about 30%, about 40%, about 45%, about 50%, or about 60% and the on-path percentage at the reaction endpoint is at least about 60%, at least about 70%, at least about 75%, or at least about 80%; or at least about 85% or at least about 90%.

contacting a separation media in a separation zone with a feed mixture comprising the glucaric acid and on-path intermediates, wherein at least a portion of the glucaric acid is separated from the on-path intermediates and a raffinate is formed comprising at least a portion of the on-path intermediates;

removing the raffinate from the separation zone; and eluting the glucaric acid from the separation media with an eluent comprising water to form the extract comprising the glucaric acid; and recycling the on-path intermediates to the oxidation reaction zone.

When the separation media is contacted with the feed mixture, at least a portion of the glucaric acid and the on-path intermediates are retained on the separation media. Also, the raffinate comprising the on-path intermediates is formed by eluting at least a portion of the on-path intermediates from the separation media with the eluent. As a result of these separation processes, the weight ratio of the glucaric acid to the on-path intermediates in the extract is greater than the weight ratio of the glucaric acid to the on-path intermediates in the feed mixture and/or the raffinate. In accordance with the present invention, the extraneous acid concentration of the eluent, prior to contact with the separation media, can be less than about 1 wt. %, less than about 0.5 wt. %, less than about 0.2 wt. %, less than about 0.1 wt. %, less than about 0.05 wt. %, or less than about 0.01 wt. % and/or the eluent is (i) makeup water and/or (ii) process water comprising water and optionally feed mixture constituents. Also, the separation media can comprise a di-carboxylate form of an anion exchange chromatography resin, more particularly the glucarate form of an anion exchange chromatography resin.

Any of the features or modifications described above can be incorporated into this process. For example, contacting the separation media with the feed mixture; removing the raffinate from the separation zone; and eluting the glucaric acid from the separation media can be performed continuously. Also, the separation zone can be a SMB chromatography stage. The separation zone can comprise a plurality of chromatography beds. Further, the SMB stage can comprise sequential SMB and/or continuous SMB chromatography.

Glucaric Acid Products

Yet another aspect of the present invention is directed to various glucaric acid products obtained from processes described herein. One glucaric acid product can be obtained from the oxidation reaction zone or subsequent concentration zone(s). Not only is this product useful as an intermediate in the production of compounds such as adipic acid, but also in commercial applications such as de-icing fluids, acidulants, detergent builders, pH regulators, chelants, descalers, corrosion inhibitors, metal cleaning and finishing agents, a component of cement formulations (concrete admixtures including water reducing and set retarding formulations). Generally, the dissolved solids of this glucaric acid product are a mixture comprising large portions of glucaric acid or salt thereof and gluconic acid or salt thereof and can optionally include lesser portions of ketogluconic acids (i.e., 2-ketogluconic acid, 3-ketogluconic acid, 4-ketogluconic acid, and 5-ketogluconic acid), $C_2$-$C_5$ di-acids (e.g., xylaric acids, tartaric acid, tartronic acid, and oxalic acid), salts of any one of the aforementioned acids, and glucose. In particular, this glucaric acid product comprises from about 30 wt. % to about 65 wt. % glucaric acid, from about 25 wt. % to about 70 wt. % gluconic acid, less than about 10 wt. % of one or more ketogluconic acids, less than about 5 wt. % of one or more $C_2$-$C_5$ di-acids, and less than about 5 wt. % glucose, wherein each weight percent is based on the dissolved solids content of the glucaric acid product. In other embodiments, products of the present invention include those in which at least a portion of the various component mon-carboxylic and di-carboxylic acids described herein are in salt form, such as in the form of a sodium, potassium, calcium, magnesium, or other salt (e.g., sodium glucarate).

The glucaric acid concentration of the glucaric acid product can be from about 20 wt. % to about 65 wt. % glucaric acid, from about 25 wt. % to about 65 wt. % glucaric acid, from about 30 wt. % to about 65 wt. % glucaric acid, from about 40 wt. % to about 65 wt. %, from about 40 wt. % to about 60 wt. %, from about 45 wt. % to about 65 wt. %, from about 45 wt. % to about 60 wt. %, from about 50 wt. % to about 65 wt. %, or from about 50 wt. % to about 60 wt. % of the dissolved solids contents. Further, the gluconic acid concentration can be from about 25 wt. % to about 65 wt. %, from about 25 wt. % to about 60 wt. %, from about 25 wt. % to about 55 wt. %, from about 25 wt. % to about 50 wt. %, from about 25 wt. % to about 45 wt. %, from about 30 wt. % to about 70 wt. %, from about 30 wt. % to about 65 wt. %, from about 30 wt. % to about 60 wt. %, from about 30 wt. % to about 55 wt. %, from about 30 wt. % to about 50 wt. %, from about 30 wt. % to about 45 wt. %, from about 30 wt. % to about 40 wt. %, or from about 50 wt. % to about 70 wt. % of the dissolved solids contents. The concentration of the ketogluconic acids can be less than about 5 wt. %, from about 1 wt. % to about 10 wt. %, or from about of 1 wt. % to about 5 wt. % of the dissolved solids contents. The concentration of the $C_2$-$C_5$ di-acids can be from about 1 wt. % to about 5 wt. % of the dissolved solids contents. Also, the glucose concentration can be less than about 2.5 wt. %, from about 0.01 wt. % to about 5 wt.

%, or from about 0.1 wt. % to about 2.5 wt. %, or from about 0.001 wt. % to about 2.5 wt. % of the dissolved solids contents.

The glucaric acid product can further comprise from about 1 wt. % to about 20 wt. %, from about 1 wt. % to about 15 wt. %, from about 1 wt. % to about 10 wt. %, from about 1 wt. % to about 5 wt. %, from about 5 wt. % to about 20 wt. %, from about 5 wt. % to about 15 wt. %, or from about 5 wt. % to about 10 wt. % guluronic acid based on the dissolved solids content. The glucaric acid product can further comprise from about 0.01 wt. % to about 1 wt. % or from about 0.01 wt. % to about 0.5 wt. % glucuronic acid based on the dissolved solids content.

In various embodiments, the glucaric acid product comprises from about 30 wt. % to about 50 wt. % glucaric acid, from about 20 wt. % to about 45 wt. % gluconic acid, from about 5 wt. % to about 15 wt. % guluronic acid, less than about 2 wt. % of glucuronic acid, less than about 6 wt. % of one or more ketogluconic acids, less than about 5 wt. % of one or more $C_2$-$C_5$ di-acids, and less than about 2 wt. % glucose, wherein each weight percent is based on the dissolved solids content of the glucaric acid product.

In some embodiments, the glucaric acid product comprises from about 35 wt. % to about 45 wt. % glucaric acid, from about 25 wt. % to about 40 wt. % gluconic acid, from about 5 wt. % to about 15 wt. % guluronic acid, less than about 2 wt. % of glucuronic acid, less than about 6 wt. % of one or more ketogluconic acids, less than about 5 wt. % of one or more $C_2$-$C_5$ di-acids, and less than about 2 wt. % glucose, wherein each weight percent is based on the dissolved solids content of the glucaric acid product.

Moreover, the glucaric acid product typically does not contain a significant fraction of undissolved solids, such as heterogeneous catalyst particles. Therefore, the glucaric acid product can have an undissolved solids content of less than about 5 wt. %, less than about 1 wt. %, or less than about 0.1 wt. % based on the total weight of the glucaric acid product.

Also, the glucaric acid product typically does not contain a significant portion of metal contaminants. Accordingly, the glucaric acid product can have a metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product. Further, the glucaric acid product can have a transition metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product. More particularly, the glucaric acid product can have a noble metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product.

Further, a concentrated glucaric acid product can be obtained from the separation zone or concentration zone(s) subsequent thereto. Not only is this product useful as an intermediate in the production of compounds such as adipic acid, but can also be used in pharmaceutical, food, and other commercial applications such as detergent builders, corrosion inhibitors, metal cleaning and finishing agents, a component of cement formulations, and metal sequestration. Generally, the dissolved solids of this concentrated glucaric acid product comprise a large portion of glucaric acid and optionally includes lesser portions of gluconic acid, ketogluconic acids (i.e., 2-ketogluconic acid, 3-ketogluconic acid, 4-ketogluconic acid, and 5-ketogluconic acid), $C_2$-$C_5$ di-acids (e.g., pentaric acids, tartaric acid, tartronic acid, and oxalic acid), and glucose. In particular, this concentrated glucaric acid product comprises from about 85 wt. % to about 99 wt. % glucaric acid, less than about 5 wt. % gluconic acid, less than about 2.5 wt. % of one or more ketogluconic acids, and less than about 10 wt. % of one or more $C_2$-$C_5$ di-acids, less than about 1 wt. % glucose, wherein each weight percent is based on the dissolved solids content of the concentrated glucaric acid product.

The glucaric acid concentration of the concentrated glucaric acid product can be from about 90 wt. % to about 99 wt. % or from about 90 wt. % to about 95 wt. % of the dissolved solids contents. The gluconic acid concentration can be from about 1 wt. % to about 5 wt. % or from about 1 wt. % to about 2.5 wt. % of the dissolved solids contents. The concentration of the ketogluconic acids can be less than about 1 wt. %, less than about 0.5 wt. %, less than about 0.1, less than about 0.01 wt. %, or from about 0.01 wt. % to about 1 wt. % of the dissolved solids contents. The concentration of the $C_2$-$C_5$ di-acids can be less than about 7.5 wt. %, less than about 5 wt. %, from about 1 wt. % to about 10 wt. %, from about 1 wt. % to about 7.5 wt. %, or from about 2.5 wt. % to about 7.5 wt. % of the dissolved solids contents. The glucose concentration can be less than about 0.5 wt. %, less than about 0.1, or less than about 0.01 wt. % of the dissolved solids contents.

The concentrated glucaric acid product can further comprise from about 0.1 wt. % to about 5 wt. % or from about 0.1 wt. % to about 2.5 wt. % guluronic acid based on the dissolved solids content.

The glucaric acid product and concentrated glucaric acid can be essentially free of nitric acid and salts thereof. For example, the glucaric acid product and concentrated glucaric acid can contain less that than about 0.1 wt. % or less than about 0.01 wt. % of nitric acid and salts thereof. The glucaric acid product and concentrated glucaric acid can be free of nitric acid and salts thereof.

As mentioned else herein, the terms "glucaric acid" "gluconic acid," and "guluronic acid" each refer collectively to the acid and any corresponding lactones that may be present. For example, the term "glucaric acid" is inclusive of glucaric acid, glucaro-1,4-lactone, glucaro-6,3-lactone, and glucaro-1,4:6,3-dilactone.

Integrated Processes

A further aspect of the present invention is directed to various integrated processes that include the separation process, separation media, and/or oxidation processes in accordance with various other aspects of the invention. For example, one process includes the selective halide-promoted hydrodeoxygenation of an aldaric acid or salt, ester, or lactone thereof to a di-carboxylic acid. As such, the present invention is also directed to a process for the selective halide promoted hydrodeoxygenation of an aldaric acid comprising reacting the aldaric acid or salt, ester, or lactone thereof that is obtained from any one of the oxidation process of the present invention with hydrogen in the presence of a halogen-containing compound and a catalyst composition as described herein to form a di-carboxylic acid. Preferred aldaric acids include glucaric acid (and lactones thereof) and xylaric acid.

Typically, the catalyst composition comprises at least one noble metal as a catalytically active component. U.S. Pat. Nos. 8,669,397 and 8,669,397 referenced above and incorporated herein by reference, describe chemocatalytic processes for the hydrodeoxygenation of glucaric acid to adipic acid and xylaric acid to glutaric acid.

Adipic acid is an especially useful industrial di-carboxylic acid. Accordingly, another process of the present invention is directed to a process for preparing adipic acid. The process comprises reacting at least a portion of the glucaric acid and lactones thereof obtained from any one of the oxidation process of the present invention with hydrogen in the presence of a halogen-containing compound and a catalyst in hydrodeoxygenation reaction zone to form adipic acid.

Adipic acid or salts and esters thereof may be prepared by reacting, in the presence of a hydrodeoxygenation catalyst and a halogen source, glucaric acid or salt, ester, or lactone thereof, and hydrogen, according to the following reaction:

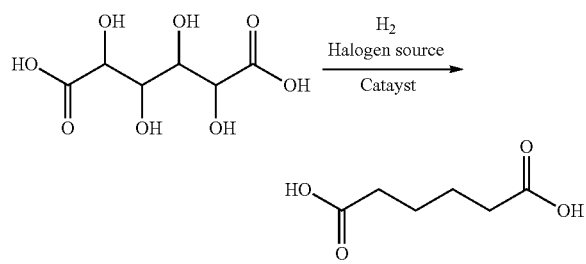

In the above reaction, glucaric acid or salt, ester, or lactone thereof is converted to an adipic acid product by catalytic hydrodeoxygenation in which carbon-hydroxyl groups are converted to carbon-hydrogen groups. In various embodiments, the catalytic hydrodeoxygenation is hydroxyl-selective wherein the reaction is completed without substantial conversion of the one or more other non-hydroxyl functional group of the substrate.

The halogen source may be in a form selected from the group consisting of ionic, molecular, and mixtures thereof. Halogen sources include hydrohalic acids (e.g., HCl, HBr, HI and mixtures thereof; preferably HBr and/or HI), halide salts, (substituted or unsubstituted) alkyl halides, or molecular (diatomic) halogens (e.g. chlorine, bromine, iodine or mixtures thereof preferably bromine and/or iodine). The halogen source can be diatomic, hydrohalic acid, or halide salt and, more preferably, diatomic form or hydrohalic acid. In certain embodiments, the halogen source is a hydrohalic acid, in particular hydrogen bromide.

Generally, the molar ratio of halogen to the glucaric acid or salt, ester, or lactone thereof is about equal to or less than about 1. The mole ratio of halogen to the glucaric acid or salt, ester, or lactone thereof can be typically from about 1:1 to about 0.1:1, more typically from about 0.7:1 to about 0.3:1, and still more typically about 0.5:1. Typically, the reaction allows for recovery of the halogen source and catalytic quantities (where molar ratio of halogen to the glucaric acid or salt, ester, or lactone thereof is less than about 1) of halogen can be used, recovered and recycled for continued use as a halogen source.

Generally, the temperature of the hydrodeoxygenation reaction mixture is at least about 20° C., typically at least about 80° C., and more typically at least about 100° C. The temperature of the hydrodeoxygenation reaction can be conducted in the range of from about 20° C. to about 250° C., from about 80° C. to about 200° C., from about 120° C. to about 180° C., or from about 140° C. to 180° C. Typically, the partial pressure of hydrogen is at least about 25 psia (172 kPa), more typically at least about 200 psia (1379 kPa) or at least about 400 psia (2758 kPa). The partial pressure of hydrogen can be from about 25 psia (172 kPa) to about 2500 psia (17237 kPa), from about 200 psia (1379 kPa) to about 2000 psia (13790 kPa), or from about 400 psia (2758 kPa) to about 1500 psia (10343 kPa).

The hydrodeoxygenation reaction may be conducted in the presence of a solvent. Solvents suitable for the selective hydrodeoxygenation reaction include water and carboxylic acids, amides, esters, lactones, sulfoxides, sulfones and mixtures thereof. Preferred solvents include water, mixtures of water and weak carboxylic acid, and weak carboxylic acid. A preferred weak carboxylic acid is acetic acid.

The catalytically active component may include noble metals selected from the group consisting of ruthenium, rhodium, palladium, platinum, and combinations thereof. The hydrodeoxygenation catalyst can comprise two or more metals. For example, the first metal can be selected from the group consisting of cobalt, nickel, ruthenium, rhodium, palladium, osmium, iridium, and platinum (more particularly, ruthenium, rhodium, palladium, and platinum) and the second metal is selected from the group consisting of titanium, vanadium, chromium, manganese, iron, cobalt, nickel, copper, molybdenum, ruthenium, rhodium, palladium, silver, tungsten, iridium, platinum, and gold (more particularly, molybdenum, ruthenium, rhodium, palladium, iridium, platinum, and gold). Preferably, the first metal can be selected from the group of platinum, rhodium and palladium, and the second metal is selected from the group consisting of ruthenium, rhodium, palladium, platinum, and gold. More preferably, the first metal is platinum and the second metal is rhodium. The platinum to rhodium molar ratio of the catalyst composition of the present invention is typically in the range of from about 3:1 to about 1:2 or from about 3:1 to about 1.1.

Having described the invention in detail, it will be apparent that modifications and variations are possible without departing from the scope of the invention defined in the appended claims.

EXAMPLES

The following non-limiting examples are provided to further illustrate the present invention.

Example 1. Oxidation of Glucose to Glucaric Acid with Moderate Single-Pass Glucaric Acid Yield and High On-Path Percentage 137.8 g of carbon black powder (Monarch 700 supplied by Cabot) was added in multiple portions to an aqueous solution (603.5 g) containing 30.7 wt. % ADM Dextrose (DE 99) and 3.3 wt. % hydroxyethylcellulose (Sigma-Aldrich, SKU 54290, 2% in $H_2O$). The mixture was stirred well to produce a paste. This paste was loaded into a syringe and the material was extruded into spaghetti-like strings with approximately 1.5 mm diameter. After drying in an 80° C. oven for 16 hours under a dry air purge, these strings were cut into small pieces about 6.0 mm long. Then they were treated at 800° C. for 2 hours after heating to 800° C. at a 5° C./min temperature ramp rate under continuous $N_2$ flow to produce carbon black extrudates.

To 91.5 g of these extrudates, an aqueous solution (32.0 ml) containing 0.73 g Au in the form of $Me_4NAuO_2$ and 1.10 g Pt in the form of $PtO(NO_3)$ was added. The mixture was agitated to impregnate the carbon black support and was dried at 70° C. under a dry air purge. The sample was then reduced at 350° C. under forming gas (5% $H_2$ and 95% $N_2$) atmosphere for 4 hours after heating to 350° C. with a 2° C./min temperature ramp rate. The final catalyst was composed of ca. 0.80 wt. % Au and 1.2 wt. % Pt. The recipes were repeated in batches to generate the quantity of material necessary for testing in the fixed bed reactor.

Testing of Au/Pt on Carbon Black Extrudate Catalyst in a Fixed-Bed Reactor for Glucose Oxidation Reactions were conducted in a 1-inch OD by 5.5 feet (66 inches) long 316 stainless steel tube with co-current down-flow feed of gas and liquid. The tube was packed with 1.0 mm glass beads at the bottom of the tube (30 cm depth), followed by catalyst (344 g, 0.80 wt. % Au+1.2 wt. % Pt on carbon black pellets) then 1.0 mm glass beads at the top to approximately 18 cm depth.

The temperature of the packed reactor tube was control through the use of an oil jacket with a continuous flow of oil connected to a reservoir equipped with temperature control. Gas (compressed dry air) and liquid flows were regulated by mass flow controller, pumps, and Coriolis flow meters, respectively. A pressure control valve is used to regulate the reactor pressure. A 30 wt. % solution of glucose was fed into the reactor under 2 different flow conditions: First flow condition=1.3 kg/hour glucose solution flow along with a stream of air at a pressure of 775 psi and a flow rate of 700 standard liters per hour. Second flow condition=0.65 kg/hr glucose solution flow along with a stream of air at a pressure of 775 psi and a flow rate of 350 standard liters per hour. Under both conditions, the catalyst bed was kept at a temperature of 140° C. Product collected from the exit of the reactor was analyzed by ion chromatography. A Dionex ICS-3000 Chromatography system equipped with Corona CAD detector (Thermo Scientific) was used. Samples were first diluted with deionized water to suitable concentrations, then separated on an Ionpac® AS11-HC column and quantified by conductivity and Corona CAD detection through comparison with calibration standards. Product analyses for representative samples collected are shown in Table 1 (molar yields). A representative sample from flow condition 1 was taken at around 1200 hours of continuous on-stream operation. For flow condition 2, a representative sample was taken after a further 50 hours on stream.

Example 2. Separation of Glucaric Acid from Gluconic Acid and other On-Path Intermediates The sequential simulated moving bed (SSMB-6) system used for this example was built by Novasep and comprised six columns in which two different streams can be fed by two pumps, and two different outlets are connected to each column. Each column is equipped with five automatic valves. Each inlet stream is flow controlled and monitored, while the outlets are pressure controlled to ensure a steady flow rate in the columns, plus one loop control with pump and flow meter. The columns are jacketed to provide accurate temperature control. For each column, two inlet valves select the feed stream (feed or eluent), one valve allows the connection to the next column, and two outlets valves select the outlet stream (extract or raffinate). The six columns are connected in series.

The resin used for the sequential SMB (SSMB) separation was Lanxess Lewatit MDS 4368, a styrene/divinylbenzene cross-linked macroporous anion exchange resin (75-80% weak-base+25-20% strong-base functionality) with 1.4 eq./L exchange capacity and 0.3 mm bead size. Before loading in the SSMB unit, the free-base and $OH^-$ forms of the resin were converted to the glucarate form through treatment with a 1 M glucaric acid solution (prepared through the hydrolysis of a solution of D-glucaro-1,4:6,3-dilactone in water at room temperature for 24 hours). After treatment, the resin was thoroughly washed with DI water (monitored by conductivity) to remove excess glucaric acid.

The resin in the glucarate form was loaded into a six column SSMB unit. Each column was 2.5 cm in diameter and 2 m in length, containing ca. 1 L of resin each. The column temperatures were regulated at 60° C. The eluent was composed of degassed and demineralized water pre-heated to 60° C. The feed solution was prepared by concentrating product from the oxidation reactor of Example 1 to 48 wt. % dissolved solids (DS) in a tubular up-flow continuous evaporator operating at 40° C. and 100 mbar vacuum. The feed was pre-heated to 60° C.

Component analysis of feed, extract and raffinate streams was conducted using ion-chromatography (IC) with conductivity and Corona CAD detection as previously described of Example 1.

Figure 2:
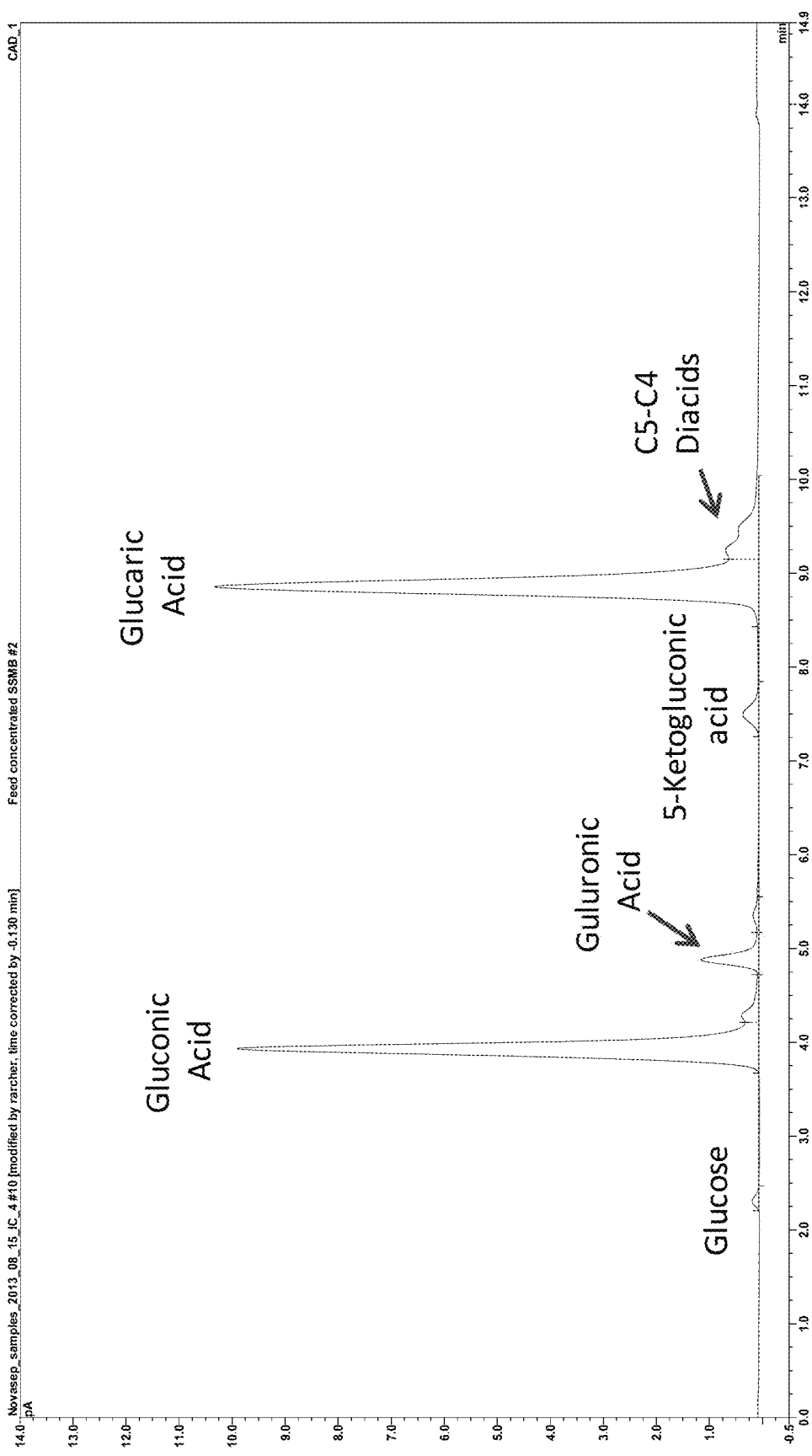
FIG. 2 depicts the ion-chromatography chromatogram for the concentrated feed in Example 2.
Figure 3:
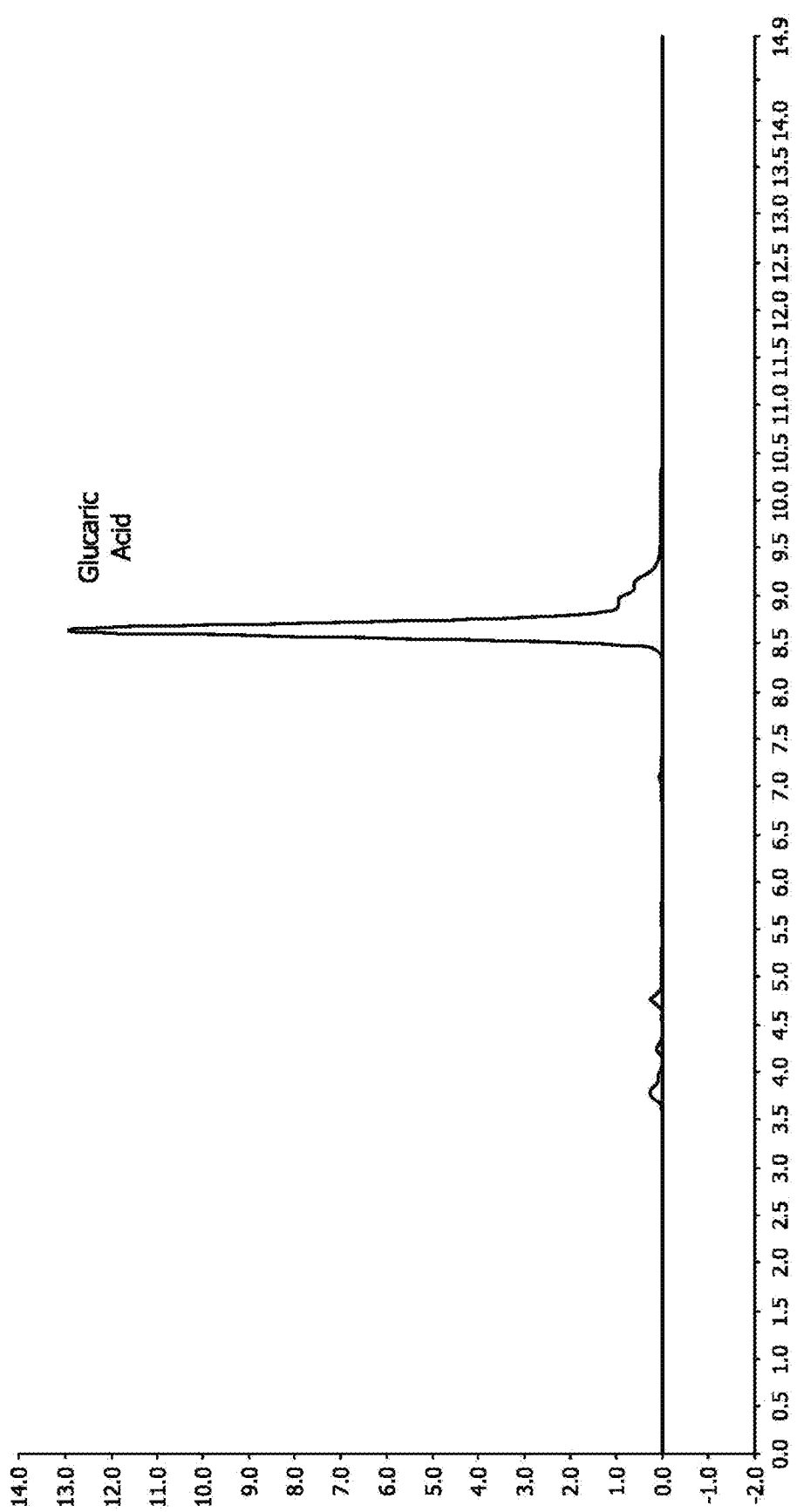
FIG. 3 depicts the ion-chromatography chromatogram for the concentrated extract stream in Example 2.

The separation was performed on 284 L of concentrated feed, collecting 920 L of extract and 330 L of raffinate, respectively. Extract and raffinate solutions from the SSMB separation were concentrated (using the same evaporation equipment and conditions as for the feed solution) to 120 L and 175 L, respectively. Tables 2, 3, and 4 show a) the mM concentrations, b) the mol % of the dissolved solids, and c) the mass balance of the components of the concentrated feed, extract, and raffinate streams. Table 5 shows the % recovery of on-path intermediates in the raffinate stream. Table 6 shows operating parameters from the SSMB, including separation productivity and eluent (water)/feed ratio. FIGS. 2 and 3 depict the ion-chromatography chromatograms for the concentrated feed and extract streams.

Table 3 shows that SSMB enabled enrichment of the glucaric acid content from 47.9 mol % in the feed solution to 90.1 mol % in the extract. In addition, Table 5 shows that the majority (97% by mass) of the unconverted glucose and on-path intermediates are concentrated in the raffinate stream, thus available for recycle back to the oxidation reactor. Table 6 shows that the SSMB separation can be accomplished with very high productivity with respect to volume of resin required per mass of product separated, conducted with a low water to feed ratio below 3.5.

TABLE 1

Product Analysis (molar yield % unless indicated)

| Flow Rate (kg/hr) | Glucose | Gluconic Acid | Glucaric Acid | Guluronic Acid | Glucuronic Acid | 2- and 3- Ketogluconic Acids | 4- and 5- Ketogluconic Acids | Sum of $C_5$-$C_2$ Di-acids | On Path Percentage (%) |
|---|---|---|---|---|---|---|---|---|---|
| 1.3 | 0.4 | 43.6 | 37.8 | 7.4 | 0.6 | 2.7 | 4.1 | 3.7 | 90 |
| 0.65 | 0 | 20.7 | 58.3 | 4.4 | 0.5 | 1.3 | 3.8 | 5.3 | 84 |

TABLE 2

Composition of Concentrated Feed, Extract and Raffinate Streams from SSMB Separation (mM)

| Sample | Glucose | Gluconic Acid | Glucaric Acid | Guluronic Acid | Glucuronic Acid | 2- and 3- Ketogluconic Acids | 4- and 5- Ketogluconic Acids | C5-Di- acid + Tartaric Acid | Tartronic Acid + Oxalic Acid |
|---|---|---|---|---|---|---|---|---|---|
| Feed | 20.7 | 1030.7 | 1285.0 | 80.8 | 12.2 | 37.2 | 50.4 | 79.6 | 19.1 |
| Extract | 0.0 | 46.1 | 2074.6 | 25.7 | 0.0 | 14.3 | 11.2 | 124.5 | 6.1 |
| Raffinate | 37.6 | 1649.7 | 567.7 | 116.3 | 7.9 | 45.6 | 73.1 | 61.3 | 0.8 |

TABLE 3

Components of Feed, Extract and Raffinate Streams from SSMB Separation (mol % of dissolved solids)

| Sample | Glucose | Gluconic Acid | Glucaric Acid | Guluronic Acid | Glucuronic Acid | 2- and 3- Ketogluconic Acids | 4- and 5- Ketogluconic Acids | C5-Di- acid + Tartaric Acid | Tartronic Acid + Oxalic Acid |
|---|---|---|---|---|---|---|---|---|---|
| Feed | 0.8 | 39.4 | 49.1 | 3.1 | 0.5 | 1.4 | 1.9 | 3.0 | 0.7 |
| Extract | 0.0 | 2.0 | 90.1 | 1.1 | 0.0 | 0.6 | 0.5 | 5.4 | 0.3 |
| Raffinate | 1.5 | 64.4 | 22.2 | 4.5 | 0.3 | 1.8 | 2.9 | 2.4 | 0.0 |

TABLE 4

Analytical Mass Balance of Feed, Extract and Raffinate Streams from SSMB Separation (kg of dissolved solids)

| Sample | Glucose | Gluconic Acid | Glucaric Acid | Guluronic Acid | Glucuronic Acid | 2- and 3- Ketogluconic Acids | 4- and 5- Ketogluconic Acids | C5-Di- acid + Tartaric Acid | Tartronic Acid + Oxalic Acid |
|---|---|---|---|---|---|---|---|---|---|
| Feed | 1.1 | 57.4 | 76.7 | 4.5 | 0.7 | 2.1 | 2.8 | 3.7 | 0.6 |
| Extract | 0.0 | 1.1 | 52.3 | 0.6 | 0.0 | 0.3 | 0.3 | 2.5 | 0.1 |
| Raffinate | 1.2 | 56.6 | 20.9 | 4.0 | 0.3 | 1.5 | 2.5 | 1.8 | 0.0 |

TABLE 5

% Recovery of On-Path Intermediates

| Sample | Glucose (kg) | Gluconic Acid (kg) | Glucuronic Acid (kg) | Glucuronic Acid (kg) | Total |
|---|---|---|---|---|---|
| Feed | 1.1 | 57.7 | 4.5 | 0.7 | 64.0 |
| Raffinate | 1.2 | 56.6 | 4.0 | 0.3 | 62.1 |
| % Recovery | 100% | 98% | 89% | 43% | 97% |

TABLE 6

SSMB Performance Metrics

| Productivity (gDS/L resin · day) | Water:Feed Ratio |
|---|---|
| 1500 | 3.4:1 |

Example 3. Overloading Test with Gluconic and Glucaric Acids Using Finex AA 543 Anion Exchange Resin in Oxalate, Glucarate, and Sulfate Forms The overloading test provides information about the competitive absorption of glucaric acid and gluconic acid on a separation resin under overloading conditions and indicates the feasibility for the resin to be deployed in an industrial simulated moving bed chromatography system.

The overloading test was conducted using the equipment listed below:
A chromatography column (1 m bed length and 2.5 cm diameter fitted with a double jacket).
A water bath connected to the chromatography column double jacket for temperature control.
A pump with a regulated flow rate control.
A feed tank.
An elution tank containing demineralized water.
A fraction collector.

The chromatography column was packed with Finex AA 543, a 400-500 µm diameter acrylic divinyl benzene weak base anion exchange resin from Finex Oy, Kotka, Finland. The oxalate, glucarate, and sulfate forms of the resin were tested. The resin was converted to the oxalate and glucarate forms by flowing a solution containing the corresponding acid (i.e., oxalic acid, glucaric acid, and sulfuric acid, respectively) through the column in an upward direction. The water bath temperature was set to 30° C. for the overloading tests.

The overloading test was conducted in two stages: (1) product loading and adsorption and (2) desorption and elution with eluent, using the protocol described as follows. Two bed volumes of a product solution containing 345 g/L glucaric acid and 181 g/L gluconic acid were pumped in down-flow mode through the column at a flow velocity of 2.5 m/hour after which the column was rinsed with 6.5 bed volumes of water also at a flow velocity of 2.5 m/hour. Fractions were collected regularly from the outlet of the column and analyzed for gluconic acid and glucaric acid concentrations using a Dionex HPLC fitted with an Ionpac AS 15 ion exchange column and a conductivity detection system calibrated with gluconic acid and glucaric acid calibration standards.

The resin performance in the overloading test was by the determination of parameters 1-4:
1) Sweet-on retention time: The bed volume (of liquid flow) corresponding to gluconic acid or glucaric acid reaching 50% of the feed concentration during the adsorption phase.
2) Sweet-off retention time: The bed volume (of liquid flow) corresponding to gluconic acid or glucaric acid reaching 50% of the feed concentration during the desorption phase.
3) The resolution: The bed volume difference between the sweet-on and sweet-off retention times of gluconic acid and glucaric acid.
4) Rinsing volume: The volume of eluent required to rinse the glucaric acid to a concentration below 10 g/L during the desorption phase Parameters 1-4 are illustrated for a representative separation in FIG. 4.

Figure 4:
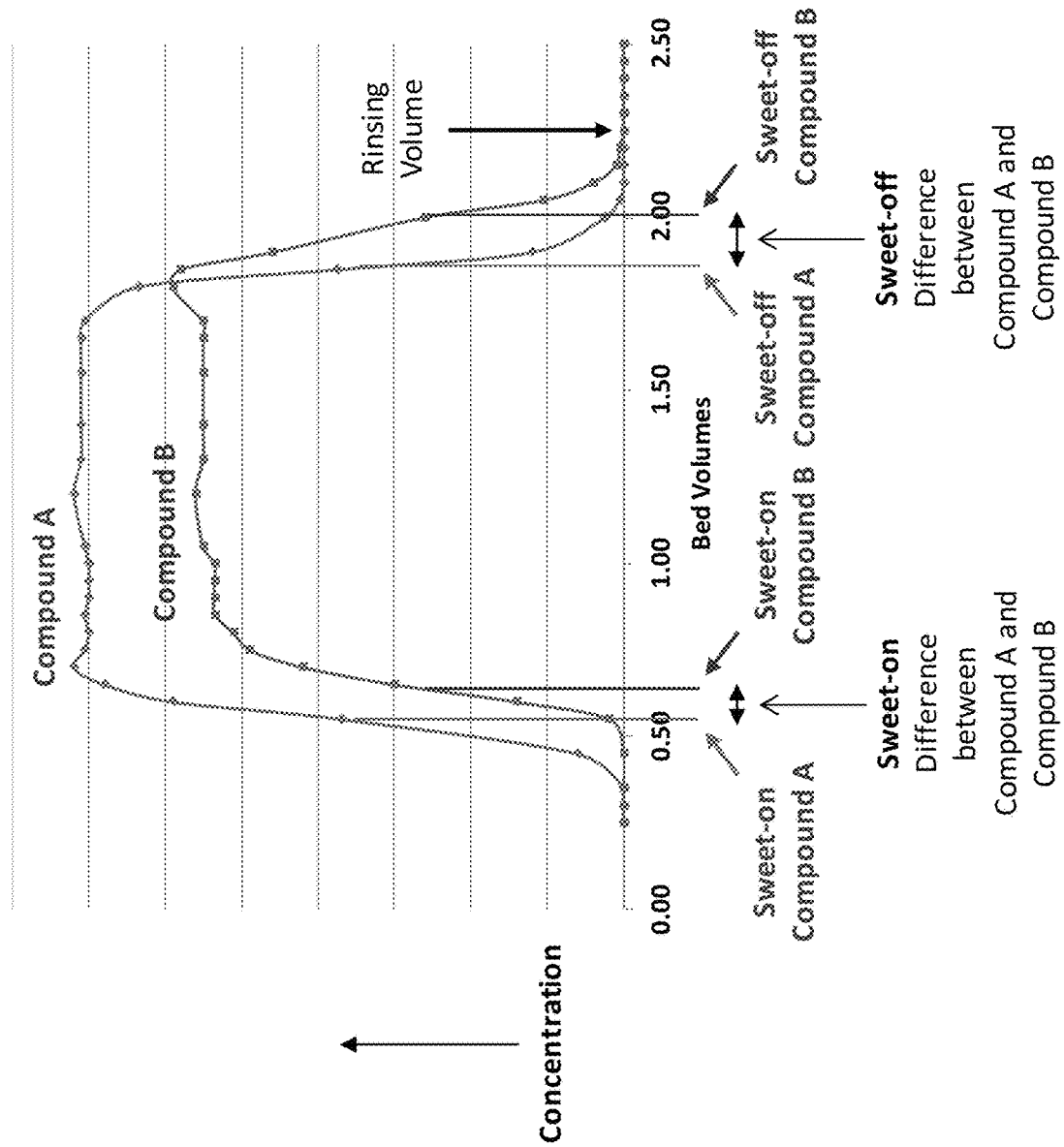
FIG. 4 presents a representative concentration profile for a separation resin operated under overloading conditions.

FIG. 4 shows that compound B is adsorbed more strongly than compound A leading to a partial separation. The sweet-on and sweet-off differences (the resolution) in FIG. 4 indicate that the resin can perform an effective separation of compound A from compound B when used in an industrial simulated moving bed chromatography system. A rinsing volume below three bed volumes will minimize the dilution of the separated compounds which is important to keep product isolation costs low.

Table 7 shows the data from the overloading test using Finex AA 543 anion exchange resin in oxalate, glucarate, and sulfate forms using water as the eluent. Table 7 demonstrates that an effective separation of gluconic acid from glucaric acid can be performed using Finex AA 543 anion exchange resin in oxalate and glucarate forms using water as the eluent.

TABLE 7

Overloading Test Results Using Finex AA 543 with Water as the Eluent

| Compound | Time period | AA 543 Oxalate Form Resin | AA 543 Glucarate Form Resin | AA 543 Sulfate Form Resin |
| --- | --- | --- | --- | --- |
| Gluconic Acid | Sweet-On (BV) | 0.74 | 0.62 | 0.62 |
|  | Sweet-Off (BV) | 2.58 | 2.58 | 2.65 |
| Glucaric Acid | Sweet-On (BV) | 0.98 | 0.85 | 0.82 |
|  | Sweet-Off (BV) | 2.90 | 2.85 | 2.85 |
| Glucaric-Gluconic Sweet-On Difference (BV) |  | 0.24 | 0.23 | 0.20 |
| Glucaric-Gluconic Sweet-Off Difference (BV) |  | 0.32 | 0.27 | 0.20 |
| Rinsing to Glucaric Acid Concentration at <10 g/L |  | 2.57 | 2.85 | 1.88 |

(BV): bed volumes

Additional overloading tests were conducted with the oxalate and glucarate forms of the following resins and using water as the eluent: Finex AA532 (a strong base anion Type 2, PS/DVB resin), Finex Ethylamine (a weak base anion, PS-DVB resin), Finex Dimethylamine (a 64% weak base anion/36% strong base anion, PS-DVB resin), Finex Butylamine (a weak base anion, PS-DVB resin), Mitsubishi UMA150 (strong base anion Type 1, PS-DVB resin), Mitsubishi WAG-M1 (weak base anion, polyacrylic DVB resin), Lanxess MDS 4368 (75-80% weak base anion/20-25% strong base anion, PS-DVB resin), Lanxess MDS 4468 (92% weak base anion/8% strong base anion, PS-DVB resin), Lanxess MDS 4568 (weak base anion, PS-DVB resin), Lanxess MDS FO36ZII (weak base anion, PS-DVB resin), and Lanxess KPN 19494 (79.5 weak base anion/20.5 weak acid cation, PS-DVB resin). The results for these resins were similar to those for Finex AA543 and demonstrate that an effective separation of gluconic acid from glucaric acid can be performed using these resins and water as the eluent.

Table 8 shows the data from the overloading test using Finex AA 543 anion exchange resin in oxalate, glucarate, and sulfate forms, but using various acid-containing solutions as the eluents (i.e., oxalic acid, glucaric acid (as a solution of glucarodilactone), and sulfuric acid).

TABLE 8

Overloading Test Results Using Finex AA 543 with Acid-Containing Solutions as the Eluents

| Compound | Time period | AA 543 Oxalate Form Resin (1 g/L oxalic acid eluent) | AA 543 Glucarate Form Resin (1 g/L glucaro dilactone eluent) | AA 543 Sulfate Form Resin (2 g/L sulfuric acid eluent) |
| --- | --- | --- | --- | --- |
| Gluconic Acid | Sweet-On (BV) | 0.62 | 0.65 | 0.60 |
| Glucaric Acid | Sweet-Off (BV) | 2.60 | 2.58 | 2.60 |
|  | Sweet-On (BV) | 0.80 | 0.85 | 0.78 |
|  | Sweet-Off (BV) | 2.85 | 2.88 | 2.80 |
| Glucaric-Gluconic Sweet-On Difference (BV) |  | 0.18 | 0.20 | 0.18 |
| Glucaric-Gluconic Sweet-Off Difference (BV) |  | 0.25 | 0.30 | 0.20 |
| Rinsing to Glucaric Acid Concentration at <10 g/L |  | 2.05 | 2.85 | 1.63 |

(BV): bed volumes

Embodiments

For further illustration, additional non-limiting embodiments of the present disclosure are set forth below.

For example, embodiment A1 is a process for producing an extract comprising a di-carboxylic acid, the process comprising:

contacting a separation media in a separation zone with a feed mixture comprising the di-carboxylic acid and a second component, wherein at least a portion of the di-carboxylic acid is separated from the second component and a raffinate is formed comprising at least a portion of the second component;

removing the raffinate from the separation zone; and eluting the di-carboxylic acid from the separation media with an eluent comprising water to form the extract comprising the di-carboxylic acid, wherein the extraneous acid concentration of the eluent, prior to contact with the separation media, is less than about 1 wt. %, less than about 0.5 wt. %, less than about 0.2 wt. %, less than about 0.1 wt. %, less than about 0.05 wt. %, or less than about 0.01 wt. %.

In any of the following embodiments, when the separation media is contacted with the feed mixture, at least a portion of the di-carboxylic acid and the second component are retained on the separation media. Also, the raffinate comprising the second component is formed by eluting at least a portion of the second component from the separation media with the eluent. As a result of these separation processes, the weight ratio of the di-carboxylic acid to the second component in the extract is greater than the weight ratio of the di-carboxylic acid to the second component in the feed mixture and/or the raffinate.

Also, although the following embodiments refer to various mono-carboxylic acids and di-carboxylic acids, processes of the present invention include those where at least a portion of these acids are in salt form, such as sodium, potassium, calcium, and magnesium salts (e.g., sodium glucarate, etc.).

Embodiment A2 is the process of embodiment A1 wherein the eluent is makeup water and/or process water obtained from concentration of the extract, raffinate or the feed mixture.

Embodiment A3 is the process of embodiment A1 or A2 wherein the eluent consists essentially of water.

Embodiment A4 is the process of any one of embodiments A1 to A3 wherein the eluent does not contain any extraneous acid.

Embodiment A5 is the process of any one of embodiments A1 to A4 wherein the eluent is water.

Embodiment A6 is the process of any one of embodiments A1 to A5 wherein the pH of the eluent is between about 5 and about 7.5 between about 5.5 and about 7.5, between about 6 and about 7.5, between about 6.5 and about 7.5, between about 5 and about 7, between about 5.5 and about 7, between about 6 and about 7, between about 6.5 and about 7, or approximately neutral.

Embodiment A7 is the process of any one of embodiments A1 to A6 wherein the separation media comprises a basic chromatography media.

Embodiment A8 is the process of embodiment A7 wherein the basic chromatography media comprises a basic chromatography resin.

Embodiment A9 is the process of embodiment A8 wherein the basic chromatography resin comprises an anion exchange chromatography resin.

Embodiment A10 is the process of embodiment A9 wherein the anion exchange chromatography resin comprises a di-carboxylate form of an anion exchange chromatography resin.

Embodiment A11 is the process of embodiment A10 wherein the di-carboxylate form of the anion exchange chromatography resin comprises a $C_2$-$C_6$ di-carboxylate form of the anion exchange chromatography resin.

Embodiment A12 is the process of embodiment A11 wherein the di-carboxylate form of the anion exchange chromatography resin comprises an aldarate form of the anion exchange chromatography resin.

Embodiment A13 is the process of embodiment A11 wherein the di-carboxylate form of the anion exchange chromatography resin is selected from the group consisting of the oxalate, tartronate, malonate, tartrate, succinate, xylarate, arabinarate, ribarate, glutarate, glucarate, adipate, and mixtures thereof.

Embodiment A14 is the process of any one of embodiments A10 to A13 wherein the di-carboxylate form of the anion exchange chromatography resin is prepared by conditioning the anion exchange chromatography resin with a di-carboxylic acid.

Embodiment A15 is the process of embodiment A14 wherein the di-carboxylic acid used to condition the anion exchange chromatography resin comprises a di-carboxylic acid that is present in the feed mixture.

Embodiment A16 is the process of embodiment A15 wherein the di-carboxylic acid used to condition the anion exchange chromatography media comprises a di-carboxylic acid that is present in the feed mixture and is also the highest concentration di-carboxylic acid in the feed mixture.

Embodiment A17 is the process of embodiment A14 or A16 wherein the di-carboxylic acid used to condition the anion exchange chromatography media comprises a di-carboxylic acid that is present in the feed mixture and is also the di-carboxylic acid with the lowest pKa in the feed mixture.

Embodiment A18 is the process of any one of embodiments A7 to A17 wherein the basic chromatography media comprises a weakly basic anion exchange chromatography resin.

Embodiment A19 is the process of any one of embodiments A7 to A18 wherein the basic chromatography media comprises from about 60% to about 100%, from about 60% to about 90%, from about 70% to about 90%, from about 70% to about 85%, from about 70% to about 80%, or from about 75% to about 80% weak base functionality.

Embodiment A20 is the process of any one of embodiments A7 to A16 wherein the basic chromatography media comprises from about 0% to about 40%, from about 10% to about 25%, from about 0% to about 10%, from about 5% to about 40%, from about 5% to about 25%, from about 5% to about 10%, from about 10% to about 40%, from about 10% to about 35%, from about 15% to about 35%, from about 15% to about 30%, from about 20% to about 30%, or from about 20% to about 25% strong base functionality.

Embodiment A21 is the process of any one of embodiments A1 to A20 wherein the extract comprises at least about 50 wt. %, at least about 60 wt. %, at least about 70 wt. %, at least about 80 wt. %, or at least about 90 wt. % of the di-carboxylic acid content of the feed mixture.

Embodiment A22 is the process of any one of embodiments A1 to A20 wherein the extract comprises from about 55 wt. % to about 100 wt. %, from about 55 wt. % to 99 wt. %, from about 55 wt. % to about 95 wt. %, from about 55 wt. % to about 90 wt. %, from about 55 wt. % to about 85 wt. %, from about 55 wt. % to about 80 wt. %, from about 60 wt. % to about 90 wt. %, from about 60 wt. % to about 85 wt. %, from about 60 wt. % to about 80 wt. %, from about 70 wt. % to about 90 wt. %, from about 70 wt. % to about 85 wt. %, or from about 70 wt. % to about 80 wt. % of the di-carboxylic acid content of the feed mixture.

Embodiment A23 is the process of any one of embodiments A1 to A22 wherein the raffinate comprises at least about 60 wt. %, at least about 70 wt. %, at least about 80 wt. %, at least about 90 wt. %, or at least about 95 wt. % of the second component content of the feed mixture.

Embodiment A24 is the process of any one of embodiments A1 to A22 wherein the raffinate comprises from about 60 wt. % to about 100 wt. %, from about 60 wt. % to about 95 wt. %, from about 60 wt. % to about 90 wt. %, from about 70 wt. % to about 100 wt. %, from about 70 wt. % to about 95 wt. %, from about 70 wt. % to about 90 wt. %, from about 80 wt. % to about 100 wt. %, from about 80 wt. % to about 95 wt. %, or from about 80 wt. % to about 90 wt. % of the second component content of the feed mixture.

Embodiment A25 is the process of any one of embodiments A1 to A24 wherein the di-carboxylic acid concentration in the feed mixture is at least about 20 wt. %, at least about 30 wt. %, at least about 40 wt. %, or at least about 50 wt. % of the dissolved solids content.

Embodiment A26 is the process of any one of embodiments A1 to A24 wherein the di-carboxylic acid concentration in the feed mixture is from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the dissolved solids content.

Embodiment A27 is the process of any one of embodiments A1 to A26 wherein the second component concentration in the feed mixture is from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the dissolved solids content.

Embodiment A28 is the process of any one of embodiments A1 to A27 wherein the second component comprises a mono-carboxylic acid.

Embodiment A29 is the process of embodiment A28 wherein the mono-carboxylic acid comprises a $C_1$ to $C_6$ mono-carboxylic acid.

Embodiment A30 is the process of any one of embodiments A1 to A29 wherein the second component comprises a mono-carboxylic acid selected from the group consisting of a $C_2$ mono-carboxylic acid, a $C_3$ mono-carboxylic acid, a $C_4$ mono-carboxylic acid, a $C_5$ mono-carboxylic acid, a $C_6$ mono-carboxylic acid, and mixtures thereof.

Embodiment A31 is the process of any one of embodiments A1 to A30 wherein the second component comprises a $C_6$ mono-carboxylic acid selected from the group consisting of gluconic acid, guluronic acid, glucuronic acid, and mixtures thereof.

Embodiment A32 is the process of any one of embodiments A1 to A31 wherein the second component comprises at least one $C_5$ aldonic acid Embodiment A33 is the process of embodiment A32 wherein the $C_5$ aldonic acid comprises at least one acid selected from the group consisting of xylonic acid, ribonic acid, arabinonic acid, and mixtures thereof.

Embodiment A34 is the process of any one of embodiments A1 to A33 wherein the second component comprises a sugar selected from the group consisting of a pentose, hexose, and mixtures thereof.

Embodiment A35 is the process of any one of embodiments A1 to A34 wherein the second component comprises glucose.

Embodiment A36 is the process of any one of embodiments A1 to A35 wherein the second component comprises a pentose.

Embodiment A37 is the process of embodiment A36 wherein the pentose comprises at least one sugar selected from the group consisting of xylose, ribose, arabinose, and mixtures thereof.

Embodiment A38 is the process of any one of embodiments A1 to A37 wherein the di-carboxylic acid comprises a $C_2$ to $C_6$ di-carboxylic acid.

Embodiment A39 is the process of embodiment A38 wherein the di-carboxylic acid comprises one or more acids selected from the group consisting of oxalic acid, tartronic acid, malonic acid, tartaric acid, succinic acid, xylaric acid, arabinaric acid, ribaric acid, glutaric acid, glucaric acid, adipic acid and mixtures thereof.

Embodiment A40 is the process of any one of embodiments A1 to A39 wherein the di-carboxylic acid comprises a $C_6$ di-carboxylic acid.

Embodiment A41 is the process of any one of embodiments A1 to A40 wherein the di-carboxylic acid comprises glucaric acid.

Embodiment A42 is the process of any one of embodiments A1 to A41 wherein the di-carboxylic acid comprises a $C_5$ di-carboxylic acid.

Embodiment A43 is the process of any one of embodiments A1 to A42 wherein the di-carboxylic acid comprises a $C_5$ aldaric acid.

Embodiment A44 is the process of embodiment A43 wherein the $C_5$ aldaric acid comprises at least one acid selected from the group consisting of xylaric acid, ribaric acid, arabinaric acid, and mixtures thereof.

Embodiment A45 is the process of any one of embodiments A1 to A44 wherein the feed mixture comprises the di-carboxylic acid and the second component dissolved in water.

Embodiment A46 is the process of any one of embodiments A1 to A45 wherein the process is a continuous separation process.

Embodiment A47 is the process of any one of embodiments A1 to A46 wherein the separation zone is a simulated moving bed chromatography stage.

Embodiment A48 is the process of embodiment A47 wherein the separation zone comprises a plurality of chromatography beds.

Embodiment A49 is the process of embodiment A47 or A48 wherein the simulated moving bed chromatography stage comprises sequential simulated moving bed chromatography.

Embodiment A50 is the process of embodiment A47 or A48 wherein the simulated moving bed chromatography stage comprises continuous simulated moving bed chromatography.

Embodiment A51 is the process of any one of embodiments A1 to A50 wherein contacting the separation media with the feed mixture; removing the raffinate from the separation zone; and eluting the di-carboxylic acid from the separation media are performed continuously.

Embodiment A52 is the process of any one of embodiments A1 to A51 wherein the dissolved solids content of the feed mixture is at least about 20 wt. %, at least about 30 wt. %, at least about 40 wt. %, or at least about 50 wt. %, or at least about 60 wt. %.

Embodiment A53 is the process of any one of embodiments A1 to A51 wherein the dissolved solids content of the feed mixture is from about 20 wt. % to about 70 wt. %, from about 20 wt. % to about 60 wt. %, from about 30 wt. % to about 70 wt. %, from about 30 wt. % to about 60 wt. %, from about 30 wt. % to about 50 wt. %, or from about 40 wt. % to about 60 wt. %.

Embodiment A54 is the process of any one of embodiments A1 to A53 wherein the extraneous acid is selected from the group comprising sulfuric acid, hydrochloric acid, acetic acid, oxalic acid and formic acid.

Embodiment A55 is the process of any one of embodiments A1 to A54 wherein the second component comprises a mixture comprising gluconic acid, guluronic acid, glucuronic acid, one or more ketogluconic acids.

Embodiment A56 is the process of any one of embodiments A1 to A55 wherein the flow rate of the eluent to the separation zone is at least about 1, at least about 10, at least about 50, at least about 100, at least about 500, at least about 1000 kg/hr, or at least 10,000 kg/hr.

Embodiment A57 is the process of any one of embodiments A1 to A56 further comprising rinsing the separation media.

Embodiment A58 is the process of any one of embodiments A1 to A57 further comprising recirculating the extract comprising the di-carboxylic acid to the separation zone.

Embodiment B1 is a process for producing an extract comprising a di-carboxylic acid, the process comprising:

contacting a separation media in a separation zone with a feed mixture comprising the di-carboxylic acid and a second component, wherein at least a portion of the di-carboxylic acid is separated from the second component and a raffinate is formed comprising at least a portion of the second component;

removing the raffinate from the separation zone; and eluting the di-carboxylic acid from the separation media with an eluent to form the extract comprising the di-carboxylic acid, wherein the eluent is (i) makeup water and/or (ii) process water comprising water and optionally feed mixture constituents.

Embodiment B2 is the process of embodiment B1 wherein the process water is water obtained from one of more stages for concentrating the extract, raffinate and/or feed mixture.

Embodiment B3 is the process of embodiment B1 or B2 wherein the concentration of feed mixture constituents in the process water is no greater than about 1 wt. %.

Embodiment B4 is the process of anyone of embodiments B1 to B3 wherein makeup water is selected from the group consisting of deionized and distilled water.

Embodiment B5 is the process of anyone of embodiments B1 to B4 wherein the eluent, prior to contact with the separation media, has an extraneous acid concentration of less than about 1 wt. %, less than about 0.5 wt. %, less than about 0.2 wt. %, less than about 0.1 wt. %, less than about 0.05 wt. %, or less than about 0.01 wt. %.

Embodiment B6 is the process of any one of embodiments B1 to B5 wherein the pH of the eluent is between about 5 and about 7.5 between about 5.5 and about 7.5, between about 6 and 7.5, between about 6.5 and 7.5, between about 5 and about 7, between about 5.5 and about 7, between about 6 and about 7, between about 6.5 and about 7, or approximately neutral.

Embodiment B7 is the process of any one of embodiments B1 to B6 wherein the separation media comprises a basic chromatography media.

Embodiment B8 is the process of embodiment B7 wherein the basic chromatography media comprises a basic chromatography resin.

Embodiment B9 is the process of embodiment B8 wherein the basic chromatography resin comprises an anion exchange chromatography resin.

Embodiment B10 is the process of embodiment B9 wherein the anion exchange chromatography resin comprises a di-carboxylate form of an anion exchange chromatography resin.

Embodiment B11 is the process of embodiment B10 wherein the di-carboxylate form of the anion exchange chromatography resin comprises a $C_2$-$C_6$ di-carboxylate form of the anion exchange chromatography resin.

Embodiment B12 is the process of embodiment B11 wherein the di-carboxylate form of the anion exchange chromatography resin comprises an aldarate form of the anion exchange chromatography resin.

Embodiment B13 is the process of embodiment B11 wherein the di-carboxylate form of the anion exchange chromatography resin is selected from the group consisting of the oxalate, tartronate, malonate, tartrate, succinate, xylarate, arabinarate, ribarate, glutarate, glucarate, adipate, and mixtures thereof.

Embodiment B14 is the process of any one of embodiments B10 to B13 wherein the di-carboxylate form of the anion exchange chromatography resin is prepared by conditioning the anion exchange chromatography resin with a di-carboxylic acid.

Embodiment B15 is the process of embodiment B14 wherein the di-carboxylic acid used to condition the anion exchange chromatography resin comprises a di-carboxylic acid that is present in the feed mixture.

Embodiment B16 is the process of embodiment B15 wherein the di-carboxylic acid used to condition the anion exchange chromatography media comprises a di-carboxylic acid that is present in the feed mixture and is also the highest concentration di-carboxylic acid in the feed mixture.

Embodiment B17 is the process of embodiment B14 or B16 wherein the di-carboxylic acid used to condition the anion exchange chromatography media comprises a di-carboxylic acid that is present in the feed mixture and is also the di-carboxylic acid with the lowest pKa in the feed mixture.

Embodiment B18 is the process of any one of embodiments B7 to B17 wherein the basic chromatography media comprises a weakly basic anion exchange chromatography resin.

Embodiment B19 is the process of any one of embodiments B7 to B18 wherein the basic chromatography media comprises from about 60% to about 100%, from about 60% to about 90%, from about 70% to about 90%, from about 70% to about 85%, from about 70% to about 80%, or from about 75% to about 80% weak base functionality.

Embodiment B20 is the process of any one of embodiments B7 to B16 wherein the basic chromatography media comprises from about 0% to about 40%, from about 10% to about 25%, from about 0% to about 10%, from about 5% to about 40%, from about 5% to about 25%, from about 5% to about 10%, from about 10% to about 40%, from about 10% to about 35%, from about 15% to about 35%, from about 15% to about 30%, from about 20% to about 30%, or from about 20% to about 25% strong base functionality.

Embodiment B21 is the process of any one of embodiments B1 to B20 wherein the extract comprises at least about 50 wt. %, at least about 60 wt. %, at least about 70 wt. %, at least about 80 wt. %, or at least about 90 wt. % of the di-carboxylic acid content of the feed mixture.

Embodiment B22 is the process of any one of embodiments B1 to B20 wherein the extract comprises from about 55 wt. % to about 100 wt. %, from about 55 wt. % to 99 wt. %, from about 55 wt. % to about 95 wt. %, from about 55 wt. % to about 90 wt. %, from about 55 wt. % to about 85 wt. %, from about 55 wt. % to about 80 wt. %, from about 60 wt. % to about 90 wt. %, from about 60 wt. % to about 85 wt. %, from about 60 wt. % to about 80 wt. %, from about 70 wt. % to about 90 wt. %, from about 70 wt. % to about 85 wt. %, or from about 70 wt. % to about 80 wt. % of the di-carboxylic acid content of the feed mixture.

Embodiment B23 is the process of any one of embodiments B1 to B22 wherein the raffinate comprises at least about 60 wt. %, at least about 70 wt. %, at least about 80 wt. %, at least about 90 wt. %, or at least about 95 wt. % of the second component content of the feed mixture.

Embodiment B24 is the process of any one of embodiments B1 to B22 wherein the raffinate comprises from about 60 wt. % to about 100 wt. %, from about 60 wt. % to about 95 wt. %, from about 60 wt. % to about 90 wt. %, from about 70 wt. % to about 100 wt. %, from about 70 wt. % to about 95 wt. %, from about 70 wt. % to about 90 wt. %, from about 80 wt. % to about 100 wt. %, from about 80 wt. % to about 95 wt. %, or from about 80 wt. % to about 90 wt. % of the second component content of the feed mixture.

Embodiment B25 is the process of any one of embodiments B1 to B24 wherein the di-carboxylic acid concentration in the feed mixture is at least about 20 wt. %, at least about 30 wt. %, at least about 40 wt. %, or at least about 50 wt. % of the dissolved solids content.

Embodiment B26 is the process of any one of embodiments B1 to B24 wherein the di-carboxylic acid concentration in the feed mixture is from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the dissolved solids content.

Embodiment B27 is the process of any one of embodiments B1 to B26 wherein the second component concentration in the feed mixture is from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the dissolved solids content.

Embodiment B28 is the process of any one of embodiments B1 to B27 wherein the second component comprises a mono-carboxylic acid.

Embodiment B29 is the process of embodiment B28 wherein the mono-carboxylic acid comprises a $C_1$ to $C_6$ mono-carboxylic acid.

Embodiment B30 is the process of any one of embodiments B1 to B29 wherein the second component comprises a mono-carboxylic acid selected from the group consisting of a $C_2$ mono-carboxylic acid, a $C_3$ mono-carboxylic acid, a $C_4$ mono-carboxylic acid, a $C_5$ mono-carboxylic acid, a $C_6$ mono-carboxylic acid, and mixtures thereof.

Embodiment B31 is the process of any one of embodiments B1 to B30 wherein the second component comprises a $C_6$ mono-carboxylic acid selected from the group consisting of gluconic acid, guluronic acid, glucuronic acid, and mixtures thereof.

Embodiment B32 is the process of any one of embodiments B1 to B31 wherein the second component comprises at least one $C_5$ aldonic acid Embodiment B33 is the process of embodiment B32 wherein the $C_5$ aldonic acid comprises at least one acid selected from the group consisting of xylonic acid, ribonic acid, arabinonic acid, and mixtures thereof.

Embodiment B34 is the process of any one of embodiments B1 to B33 wherein the second component comprises a sugar selected from the group consisting of a pentose, hexose, and mixtures thereof.

Embodiment B35 is the process of any one of embodiments B1 to B34 wherein the second component comprises glucose.

Embodiment B36 is the process of any one of embodiments B1 to B35 wherein the second component comprises a pentose.

Embodiment B37 is the process of embodiment B36 wherein the pentose comprises at least one sugar selected from the group consisting of xylose, ribose, arabinose, and mixtures thereof.

Embodiment B38 is the process of any one of embodiments B1 to B37 wherein the di-carboxylic acid comprises a $C_2$ to $C_6$ di-carboxylic acid.

Embodiment B39 is the process of embodiment B38 wherein the di-carboxylic acid comprises one or more acids selected from the group consisting of oxalic acid, tartronic acid, malonic acid, tartaric acid, succinic acid, xylaric acid, arabinaric acid, ribaric acid, glutaric acid, glucaric acid, adipic acid and mixtures thereof.

Embodiment B40 is the process of any one of embodiments B1 to B39 wherein the di-carboxylic acid comprises a $C_6$ di-carboxylic acid.

Embodiment B41 is the process of any one of embodiments B1 to B40 wherein the di-carboxylic acid comprises glucaric acid.

Embodiment B42 is the process of any one of embodiments B1 to B41 wherein the di-carboxylic acid comprises a $C_5$ di-carboxylic acid.

Embodiment B43 is the process of any one of embodiments B1 to B42 wherein the di-carboxylic acid comprises a $C_5$ aldaric acid.

Embodiment B44 is the process of embodiment B43 wherein the $C_5$ aldaric acid comprises at least one acid selected from the group consisting of xylaric acid, ribaric acid, arabinaric acid, and mixtures thereof.

Embodiment B45 is the process of any one of embodiments B1 to B44 wherein the feed mixture comprises the di-carboxylic acid and the second component dissolved in water.

Embodiment B46 is the process of any one of embodiments B1 to B45 wherein the process is a continuous separation process.

Embodiment B47 is the process of any one of embodiments B1 to B46 wherein the separation zone is a simulated moving bed chromatography stage.

Embodiment B48 is the process of embodiment B47 wherein the separation zone comprises a plurality of chromatography beds.

Embodiment B49 is the process of embodiment B47 or B48 wherein the simulated moving bed chromatography stage comprises sequential simulated moving bed chromatography.

Embodiment B50 is the process of embodiment B47 or B48 wherein the simulated moving bed chromatography stage comprises continuous simulated moving bed chromatography.

Embodiment B51 is the process of any one of embodiments B1 to B50 wherein contacting the separation media with the feed mixture; removing the raffinate from the separation zone; and eluting the di-carboxylic acid from the separation media are performed continuously.

Embodiment B52 is the process of any one of embodiments B1 to B51 wherein the dissolved solids content of the feed mixture is at least about 20 wt. %, at least about 30 wt. %, at least about 40 wt. %, or at least about 50 wt. %, or at least about 60 wt. %.

Embodiment B53 is the process of any one of embodiments A1 to B51 wherein the dissolved solids content of the feed mixture is from about 20 wt. % to about 70 wt. %, from about 20 wt. % to about 60 wt. %, from about 30 wt. % to about 70 wt. %, from about 30 wt. % to about 60 wt. %, from about 30 wt. % to about 50 wt. %, or from about 40 wt. % to about 60 wt. %.

Embodiment B54 is the process of any one of embodiments B5 to B53 wherein the extraneous acid comprises sulfuric acid, hydrochloric acid, acetic acid, oxalic acid and formic acid.

Embodiment B55 is the process of any one of embodiments B1 to B54 wherein the second component comprises a mixture comprising gluconic acid, guluronic acid, glucuronic acid, and one or more ketogluconic acids.

Embodiment B56 is the process of any one of embodiments B1 to B55 wherein the flow rate of the eluent to the separation zone is at least about 1, at least about 10, at least about 50, at least about 100, at least about 500, at least about 1000 kg/hr, or at least 10,000 kg/hr.

Embodiment B57 is the process of any one of embodiments B1 to B56 further comprising rinsing the separation media.

Embodiment B58 is the process of any one of embodiments B1 to B57 further comprising recirculating the extract comprising the di-carboxylic acid to the separation zone.

Embodiment C1 is a process for producing an extract comprising a di-carboxylic acid, the process comprising:

contacting a separation media in a separation zone with a feed mixture comprising the di-carboxylic acid and a second component, wherein at least a portion of the di-carboxylic acid is separated from the second component and a raffinate is formed comprising at least a portion of the second component;

removing the raffinate from the separation zone; and eluting the di-carboxylic acid from the separation media with an eluent comprising water to form the extract comprising the di-carboxylic acid, wherein the separation media comprises a di-carboxylate form of an anion exchange chromatography resin.

Embodiment C2 is the process of embodiment C1 wherein the di-carboxylate form of the anion exchange chromatography resin comprises a $C_2$-$C_6$ di-carboxylate form of the anion exchange chromatography resin.

Embodiment C3 is the process of embodiment C1 or C2 wherein the di-carboxylate form of the anion exchange chromatography resin comprises an aldarate form of the anion exchange chromatography resin.

Embodiment C4 is the process of embodiment C2 wherein the di-carboxylate form of the anion exchange chromatography resin comprises a form selected from the group consisting of the oxalate, tartronate, malonate, tartrate, succinate, xylarate, arabinarate, ribarate, glutarate, glucarate, adipate, and mixtures thereof.

Embodiment C5 is the process of any one of embodiments C1 to C4 wherein the di-carboxylate form of the anion exchange chromatography resin is prepared by conditioning the anion exchange chromatography resin with a di-carboxylic acid.

Embodiment C6 is the process of embodiment C5 wherein the di-carboxylic acid used to condition the anion exchange chromatography resin comprises a di-carboxylic acid that is present in the feed mixture.

Embodiment C7 is the process of embodiment C6 wherein the di-carboxylic acid used to condition the anion exchange chromatography media comprises a di-carboxylic acid that is present in the feed mixture and is also the highest concentration di-carboxylic acid in the feed mixture.

Embodiment C8 is the process of embodiment C6 or C7 wherein the di-carboxylic acid used to condition the anion exchange chromatography media comprises a di-carboxylic acid that is present in the feed mixture and is also the di-carboxylic acid that is the di-carboxylic acid with the lowest pKa in the feed mixture.

Embodiment C9 is the process of any one of embodiments C1 to C8 wherein the anion exchange chromatography resin comprises a weakly basic anion exchange chromatography resin.

Embodiment C10 is the process of any one of embodiments C1 to C9 wherein the anion exchange chromatography resin comprises from about 60% to about 100%, from about 60% to about 90%, from about 70% to about 90%, from about 70% to about 85%, from about 70% to about 80%, or from about 75% to about 80% weak base functionality.

Embodiment C11 is the process of any one of embodiments C1 to C10 wherein the anion exchange chromatography resin comprises from about 0% to about 40%, from about 10% to about 25%, from about 0% to about 10%, from about 5% to about 40%, from about 5% to about 25%, from about 5% to about 10%, from about 10% to about 40%, from about 10% to about 35%, from about 15% to about 35%, from about 15% to about 30%, from about 20% to about 30%, or from about 20% to about 25% strong base functionality.

Embodiment C12 is the process of any one of embodiments C1 to C11 wherein the extract comprises at least about 50 wt. %, at least about 60 wt. %, at least about 70 wt. %, at least about 80 wt. %, or at least about 90 wt. % of the di-carboxylic acid content of the feed mixture.

Embodiment C13 is the process of any one of embodiments C1 to C11 wherein the extract comprises from about 55 wt. % to about 100 wt. %, from about 55 wt. % to 99 wt. %, from about 55 wt. % to about 95 wt. %, from about 55 wt. % to about 90 wt. %, from about 55 wt. % to about 85 wt. %, from about 55 wt. % to about 80 wt. %, from about 60 wt. % to about 90 wt. %, from about 60 wt. % to about 85 wt. %, from about 60 wt. % to about 80 wt. %, from about 70 wt. % to about 90 wt. %, from about 70 wt. % to about 85 wt. %, or from about 70 wt. % to about 80 wt. % of the di-carboxylic acid content of the feed mixture.

Embodiment C14 is the process of any one of embodiments C1 to C13 wherein the raffinate comprises at least about 60 wt. %, at least about 70 wt. %, at least about 80 wt. %, at least about 90 wt. %, or at least about 95 wt. % of the second component content of the feed mixture.

Embodiment C15 is the process of any one of embodiments C1 to C13 wherein the raffinate comprises from about 60 wt. % to about 100 wt. %, from about 60 wt. % to about 95 wt. %, from about 60 wt. % to about 90 wt. %, from about 70 wt. % to about 100 wt. %, from about 70 wt. % to about 95 wt. %, from about 70 wt. % to about 90 wt. %, from about 80 wt. % to about 100 wt. %, from about 80 wt. % to about 95 wt. %, or from about 80 wt. % to about 90 wt. % of the second component content of the feed mixture.

Embodiment C16 is the process of any one of embodiments C1 to C15 wherein the di-carboxylic acid concentration in the feed mixture is at least about 20 wt. %, at least about 30 wt. %, at least about 40 wt. %, or at least about 50 wt. % of the dissolved solids content.

Embodiment C17 is the process of any one of embodiments C1 to C15 wherein the di-carboxylic acid concentration in the feed mixture is from about 20 wt. % to about 70 wt. %, from about 20 wt. % to about 60 wt. %, from about 30 wt. % to about 70 wt. %, from about 30 wt. % to about 60 wt. %, from about 40 wt. % to about 70 wt. %, or from about 40 wt. % to about 60 wt. % of the dissolved solids content.

Embodiment C18 is the process of any one of embodiments C1 to C17 wherein the second component concentration in the feed mixture is from about 10 wt. % to about 80 wt. %, from about 20 wt. % to about 80 wt. %, from about 30 wt. % to about 80 wt. %, from about 20 wt. % to about 50 wt. %, from about 30 wt. % to about 50 wt. %, from about 30 wt. % to about 40 wt. %, from about 35 wt. % to about 50 wt. %, or from about 35 wt. % to about 45 wt. % of the dissolved solids content.

Embodiment C19 is the process of any one of embodiments C1 to C18 wherein the second component comprises a mono-carboxylic acid.

Embodiment C20 is the process of embodiment C19 wherein the mono-carboxylic acid comprises a $C_1$ to $C_6$ mono-carboxylic acid.

Embodiment C21 is the process of any one of embodiments C1 to C20 wherein the second component comprises a mono-carboxylic acid selected from the group consisting of a $C_2$ mono-carboxylic acid, a $C_3$ mono-carboxylic acid, a $C_4$ mono-carboxylic acid, a $C_5$ mono-carboxylic acid, a $C_6$ mono-carboxylic acid, and mixtures thereof.

Embodiment C22 is the process of any one of embodiments C1 to C21 wherein the second component comprises a $C_6$ mono-carboxylic acid selected from the group consisting of gluconic acid, guluronic acid, glucuronic acid, and mixtures thereof.

Embodiment C23 is the process of any one of embodiments C1 to C22 wherein the second component comprises at least one $C_5$ aldonic acid Embodiment C24 is the process of embodiment C23 wherein the $C_5$ aldonic acid comprises at least one acid selected from the group consisting of xylonic acid, ribonic acid, arabinonic acid, and mixtures thereof.

Embodiment C25 is the process of any one of embodiments C1 to C24 wherein the second component comprises a sugar selected from the group consisting of a pentose, hexose, and mixtures thereof.

Embodiment C26 is the process of any one of embodiments C1 to C25 wherein the second component comprises glucose.

Embodiment C27 is the process of any one of embodiments C1 to C26 wherein the second component comprises a pentose.

Embodiment C28 is the process of embodiment C27 wherein the pentose comprises at least one sugar selected from the group consisting of xylose, ribose, arabinose, and mixtures thereof.

Embodiment C29 is the process of any one of embodiments C1 to C28 wherein the di-carboxylic acid comprises a $C_2$ to $C_6$ di-carboxylic acid.

Embodiment C30 is the process of embodiment C29 wherein the di-carboxylic acid comprises one or more acids selected from the group consisting of oxalic acid, tartronic acid, malonic acid, tartaric acid, succinic acid, xylaric acid, arabinaric acid, ribaric acid, glutaric acid, glucaric acid, adipic acid and mixtures thereof.

Embodiment C31 is the process of any one of embodiments C1 to C30 wherein the di-carboxylic acid comprises a $C_6$ di-carboxylic acid.

Embodiment C32 is the process of any one of embodiments C1 to C31 wherein the di-carboxylic acid comprises glucaric acid.

Embodiment C33 is the process of any one of embodiments C1 to C32 wherein the di-carboxylic acid comprises a $C_5$ di-carboxylic acid.

Embodiment C34 is the process of any one of embodiments C1 to C33 wherein the di-carboxylic acid comprises a $C_5$ aldaric acid.

Embodiment C35 is the process of embodiment C34 wherein the $C_5$ aldaric acid comprises at least one acid selected from the group consisting of xylaric acid, ribaric acid, arabinaric acid, and mixtures thereof.

Embodiment C36 is the process of any one of embodiments C1 to C35 wherein the feed mixture comprises the di-carboxylic acid and the second component dissolved in water.

Embodiment C37 is the process of any one of embodiments C1 to C36 wherein the process is a continuous separation process.

Embodiment C38 is the process of any one of embodiments C1 to C37 wherein the separation zone is a simulated moving bed chromatography stage.

Embodiment C39 is the process of embodiment C38 wherein the separation zone comprises a plurality of chromatography beds.

Embodiment C40 is the process of embodiment C38 or C39 wherein the simulated moving bed chromatography stage comprises sequential simulated moving bed chromatography.

Embodiment C41 is the process of embodiment C38 or C39 wherein the simulated moving bed chromatography stage comprises continuous simulated moving bed chromatography.

Embodiment C42 is the process of any one of embodiments C1 to C41 wherein contacting the separation media with the feed mixture; removing the raffinate from the separation zone; and eluting the di-carboxylic acid from the separation media are performed continuously.

Embodiment C43 is the process of any one of embodiments C1 to C42 wherein the dissolved solids content of the feed mixture is at least about 20 wt. %, at least about 30 wt. %, at least about 40 wt. %, or at least about 50 wt. %, or at least about 60 wt. %.

Embodiment C44 is the process of any one of embodiments C1 to C42 wherein the dissolved solids content of the feed mixture is from about 20 wt. % to about 70 wt. %, from about 20 wt. % to about 60 wt. %, from about 30 wt. % to about 70 wt. %, from about 30 wt. % to about 60 wt. %, from about 30 wt. % to about 50 wt. %, or from about 40 wt. % to about 60 wt. %.

Embodiment C45 is the process of any one of embodiments C1 to C44 wherein the second component comprises a mixture comprising gluconic acid, guluronic acid, glucuronic acid, and one or more ketogluconic acids.

Embodiment C46 is the process of any one of embodiments C1 to C45 wherein the flow rate of the eluent to the separation zone is at least about 1, at least about 10, at least about 50, at least about 100, at least about 500, at least about 1000 kg/hr, or at least 10,000 kg/hr.

Embodiment C47 is the process of any one of embodiments C1 to C46 further comprising rinsing the separation media.

Embodiment C48 is the process of any one of embodiments C1 to C47 further comprising recirculating the extract comprising the di-carboxylic acid to the separation zone.

Embodiment D1 is a process for preparing an aldaric acid, the process comprising:

oxidizing an aldose with oxygen in the presence of an oxidation catalyst in an oxidation reaction zone to form an oxidation product comprising the aldaric acid and on-path intermediates to the aldaric acid;

removing the oxidation product from the presence of the oxidation catalyst; and producing an extract comprising the aldaric acid as set forth in any of embodiments A1-A58, B1-B58, or C1-C48, wherein the feed mixture comprises the aldaric acid as the di-carboxylic acid and on-path intermediates to the aldaric acid as the second component obtained from the oxidation product.

Embodiment D2 is the process of embodiment D1, further comprising recycling the on-path intermediates to the oxidation reaction zone.

Embodiment D3 is the process of embodiment D1 or D2 wherein the aldaric acid comprises a $C_5$ or $C_6$ acid selected from the group consisting of xylaric acid, glucaric acid and mixtures thereof.

Embodiment E1 is a process for preparing glucaric acid, the process comprising:

reacting glucose with oxygen in the presence of an oxidation catalyst in an oxidation reaction zone to form an oxidation product comprising glucaric acid and on-path intermediates to glucaric acid;

removing the oxidation product from the presence of the oxidation catalyst; and producing an extract comprising glucaric acid as set forth in any of embodiments A1-A58, B1-B58, or C1-C48, wherein the feed mixture comprises glucaric acid as the di-carboxylic acid and on-path intermediates to glucaric acid as the second component obtained from the oxidation product.

Embodiment E2 is the process of embodiment E1 wherein the oxidation product is removed from the presence of the oxidation catalyst at a reaction endpoint wherein the molar yield of glucaric acid and lactones thereof at the reaction endpoint does not exceed about 30%, about 40%, about 45%, about 50%, or about 60%.

Embodiment E3 is the process of embodiment E1 wherein the oxidation product is removed from the presence of the oxidation catalyst at a reaction endpoint wherein the molar yield of glucaric acid and lactones thereof at the reaction endpoint is from about 30% to about 65%, from about 30% to about 60%, from about 30% to about 50%, from about 40% to about 65%, from about 40% to about 60%, from about 50% to about 65%, or from about 50% to about 60%

Embodiment E4 is the process of any one of embodiments E1 to E3 wherein the oxidation product is removed from the presence of the oxidation catalyst at a reaction endpoint wherein the on-path percentage at the reaction endpoint, which is the sum of (a) the molar yields of glucaric acid, gluconic acid, guluronic acid, and glucuronic acid and (b) the percentage of unconverted glucose, is at least about 60%, at least about 70%, at least about 75%, or at least about 80%, at least about 85%, or at least about 90%.

Embodiment E5 is the process of any one of embodiments E1 to E3 wherein the oxidation product is removed from the presence of the oxidation catalyst at a reaction endpoint wherein the on-path percentage at the reaction endpoint, which is the sum of (a) the molar yields of glucaric acid, gluconic acid, guluronic acid, and glucuronic acid and (b) the percentage of unconverted glucose, is from about 60% to about 100%, from about 65% to about 100%, from about 70% to about 100%, from about 60% to about 99%, from about 65% to about 99%, from about 70% to about 99%, from about 60% to about 95%, from about 65% to about 95%, or from about 70% to about 95%.

Embodiment E6 is the process of any one of embodiments E1 to E5, further comprising recycling the on-path intermediates to the oxidation reaction zone.

Embodiment E7 is the process of any one of embodiments E1 to E6 wherein unconverted glucose is recycled with the on-path intermediates to the oxidation reaction zone.

Embodiment F1 is a process for preparing glucaric acid, the process comprising:

reacting glucose with oxygen in the presence of an oxidation catalyst in an oxidation reaction zone to form an oxidation product comprising glucaric acid and on-path intermediates to glucaric acid;

removing the oxidation product from the presence of the oxidation catalyst at a reaction endpoint wherein the molar yield of glucaric acid and lactones thereof at the reaction endpoint does not exceed about 30%, about 40%, about 45%, about 50%, or about 60% and the on-path percentage at the reaction endpoint, which is the sum of (a) the molar yields of glucaric acid, gluconic acid, guluronic acid, and glucuronic acid and (b) the percentage of unconverted glucose, is at least about 60%, at least about 70%, at least about 75%, or at least about 80%, at least about 85%, or at least about 90%;

separating a glucaric acid product from on-path intermediates to glucaric acid obtained in the oxidation product; and recycling the on-path intermediates to the oxidation reaction zone.

Embodiment F2 is the process of embodiment F1 wherein the oxidation product is removed from the presence of the oxidation catalyst at a reaction endpoint wherein the molar yield of glucaric acid and lactones thereof at the reaction endpoint is from about 30% to about 65%, from about 30% to about 60%, from about 30% to about 50%, from about 40% to about 65%, from about 40% to about 60%, from about 50% to about 65%, or from about 50% to about 60%

Embodiment F3 is the process of embodiment F1 or F2 wherein the oxidation product is removed from the presence of the oxidation catalyst at a reaction endpoint wherein the on-path percentage at the reaction endpoint is from about 60% to about 100%, from about 65% to about 100%, from about 70% to about 100%, from about 60% to about 99%, from about 65% to about 99%, from about 70% to about 99%, from about 60% to about 95%, from about 65% to about 95%, or from about 70% to about 95%.

Embodiment F4 is the process of any one of embodiments F1 to F3 wherein unconverted glucose is recycled with the on-path intermediates to the oxidation reaction zone.

Embodiment F5 is the process of any one of embodiments F1 to F3 wherein the glucaric acid product is an extract produced in accordance with a separation process as set forth in any of embodiments A1-A58, B1-B58, or C1-C48, wherein the feed mixture comprises glucaric acid as the di-carboxylic acid and on-path intermediates to glucaric acid as the second component obtained from the oxidation product.

Embodiment G1 is a separation media comprising an anion exchange chromatography resin in the di-carboxylate form.

Embodiment G2 is the separation media of embodiment G1 wherein the di-carboxylate form of the anion exchange chromatography resin comprises a $C_2$-$C_6$ di-carboxylate form of the anion exchange chromatography resin.

Embodiment G3 is the separation media of embodiment G1 wherein the di-carboxylate form of the anion exchange chromatography resin comprises an aldarate form of the anion exchange chromatography resin.

Embodiment G4 is the separation media of embodiment G2 wherein the di-carboxylate form of the anion exchange chromatography resin is a form selected from the group consisting of the oxalate, tartronate, malonate, tartrate, succinate, xylarate, arabinarate, ribarate, glutarate, glucarate, adipate, and mixtures thereof.

Embodiment G5 is the separation media of embodiment G4 wherein the form of the anion exchange chromatography resin is the glucarate form.

Embodiment G6 is the separation media of embodiment G4 wherein the form of the anion exchange chromatography resin is the xylarate form.

Embodiment G7 is the separation media of any one of embodiments G1 to G6 wherein the resin comprises a styrene-divinylbenzene (DVB) copolymer.

Embodiment G8 is the separation media of any one of embodiments G1 to G6 wherein the resin comprises a cross-linked polymer or copolymer of acrylonitrile, acrylic acid, or methacrylic acid.

Embodiment G9 is the separation media of any one of embodiments G1 to G8 wherein the resin comprises an acrylate-divinylbenzene (DVB) copolymer or methyl acrylate-divinylbenzene (DVB) copolymer.

Embodiment H1 is a process for preparing adipic acid, the process comprising:

reacting at least a portion of the glucaric acid and lactones thereof obtained in the process of any one of embodiments E1 to E7 or F1 to F4 with hydrogen in the presence of a halogen-containing compound and a catalyst in hydrodeoxygenation reaction zone to form adipic acid.

Embodiment I1 is a glucaric acid product comprising:
from about 20 wt. % to about 65 wt. % glucaric acid,
from about 25 wt. % to about 70 wt. % gluconic acid,
less than about 10 wt. % of one or more ketogluconic acids,
less than about 5 wt. % of one or more $C_2$-$C_5$ di-acids, and
less than about 5 wt. % glucose, wherein each weight percent is based on the dissolved solids content of the glucaric acid product.

Embodiment I2 is the glucaric acid product of embodiment I1 further comprising from about 1 wt. % to about 10 wt. % or from about 1 wt. % to about 5 wt. % guluronic acid based on the dissolved solids content.

Embodiment I3 is the glucaric acid product of embodiment I1 or I2 wherein the glucaric acid concentration is from about 25 wt. % to about 65 wt. % glucaric acid, from about 30 wt. % to about 65 wt. % glucaric acid, from about 40 wt. % to about 65 wt. %, from about 40 wt. % to about 60 wt. %, from about 45 wt. % to about 65 wt. %, from about 45 wt. % to about 60 wt. %, from about 50 wt. % to about 65 wt. %, or from about 50 wt. % to about 60 wt. % of the dissolved solids contents.

Embodiment I4 is the glucaric acid product of any one of embodiments I1 to I3 wherein the gluconic acid concentration is from about 25 wt. % to about 65 wt. %, from about 25 wt. % to about 60 wt. %, from about 25 wt. % to about 55 wt. %, from about 25 wt. % to about 50 wt. %, from about 25 wt. % to about 45 wt. %, from about 30 wt. % to about 70 wt. %, from about 30 wt. % to about 65 wt. %, from about 30 wt. % to about 60 wt. %, from about 30 wt. % to about 55 wt. %, from about 30 wt. % to about 50 wt. %, from about 30 wt. % to about 45 wt. %, from about 30 wt. % to about 40 wt. %, or from about 50 wt. % to about 70 wt. % of the dissolved solids contents Embodiment I5 is the glucaric acid product of any one of embodiments I1 to I4 wherein the concentration of the ketogluconic acids is less than about 5 wt. %, from about 1 wt. % to about 10 wt. %, or from about of 1 wt. % to about 5 wt. % of the dissolved solids contents.

Embodiment I6 is the glucaric acid product of any one of embodiments I1 to I5 wherein the ketogluconic acids are 2-ketogluconic acid, 3-ketogluconic acid, 4-ketogluconic acid, and 5-ketogluconic acid.

Embodiment I7 is the glucaric acid product of any one of embodiments I1 to I6 wherein the concentration of the $C_2$-$C_5$ di-acids is from about 1 wt. % to about 5 wt. % of the dissolved solids contents.

Embodiment I8 is the glucaric acid product of any one of embodiments I1 to I7 wherein the glucose concentration is less than about 2.5 wt. %, from about 0.01 wt. % to about 5 wt. %, or from about 0.1 wt. % to about 2.5 wt. %, or from about 0.001 wt. % to about 2.5 wt. % of the dissolved solids contents.

Embodiment I9 is the glucaric acid product of any one of embodiments I1 to I8 wherein the $C_2$-$C_5$ di-acids comprise xylaric acid, tartaric acid, tartronic acid, and oxalic acid.

Embodiment I10 is the glucaric acid product of any one of embodiments I1 to I9 further comprising from about 0.01 wt. % to about 1 wt. % or from about 0.01 wt. % to about 0.5 wt. % glucuronic acid based on the dissolved solids content.

Embodiment I11 is the glucaric acid product of any one of embodiments I1 to I10 wherein the glucaric acid product has an undissolved solids content of less than about 5 wt. %, less than about 1 wt. %, or less than about 0.1 wt. % based on the total weight of the glucaric acid product.

Embodiment I12 is the glucaric acid product of any one of embodiments I1 to I11 wherein the glucaric acid product has a metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product.

Embodiment I13 is the glucaric acid product of any one of embodiments I1 to I12 wherein the glucaric acid product has a transition metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product.

Embodiment I14 is the glucaric acid product of any one of embodiments I1 to I13 wherein the glucaric acid product has a noble metal content of less than about 1 wt. %, less than about 0.1 wt. %, less than about 0.01 wt. %, less than about 0.001 wt. %, less than about 1 ppm, or less than about 0.1 ppm based on the total weight of the glucaric acid product.

Embodiment J1 is a concentrated glucaric acid product comprising:
from about 85 wt. % to about 99 wt. % glucaric acid,
less than about 5 wt. % gluconic acid,
less than about 2.5 wt. % of one or more ketogluconic acids,
less than about 10 wt. % or one or more $C_2$-$C_5$ di-acids, and
less than about 1 wt. % glucose, wherein each weight percent is based on the dissolved solids content of the concentrated glucaric acid product.

Embodiment J2 is the concentrated glucaric acid product of embodiment J1 further comprising from about 0.1 wt. % to about 5 wt. % or from about 0.1 wt. % to about 2.5 wt. % guluronic acid based on the dissolved solids content.

Embodiment J3 is the concentrated glucaric acid product of embodiment J1 or J2 wherein the glucaric acid concentration is from about 90 wt. % to about 99 wt. % or from about 90 wt. % to about 95 wt. % of the dissolved solids contents.

Embodiment J4 is the concentrated glucaric acid product of any one of embodiments J1 to J3 wherein the gluconic acid concentration is from about 1 wt. % to about 5 wt. % or from about 1 wt. % to about 2.5 wt. % of the dissolved solids contents.

Embodiment J5 is the concentrated glucaric acid product of any one of embodiments J1 to J4 wherein the concentration of the ketogluconic acids is less than about 1 wt. %, less than about 0.5 wt. %, less than about 0.1, less than about 0.01 wt. %, or from about 0.01 wt. % to about 1 wt. % of the dissolved solids contents.

Embodiment J6 is the concentrated glucaric acid product of any one of embodiments J1 to J5 wherein the ketogluconic acids are a mixture of 2-ketogluconic acid, 3-ketogluconic acid, 4-ketogluconic acid, and 5-ketogluconic acid.

Embodiment J7 is the concentrated glucaric acid product of any one of embodiments J1 to J6 wherein the concentration of the $C_2$-$C_5$ di-acids is less than about 7.5 wt. %, less than about 5 wt. %, from about 1 wt. % to about 10 wt. %, from about 1 wt. % to about 7.5 wt. %, or from about 2.5 wt. % to about 7.5 wt. % of the dissolved solids contents.

Embodiment J8 is the concentrated glucaric acid product of any one of embodiments J1 to J7 wherein the glucose concentration is less than about 0.5 wt. %, less than about 0.1, or less than about 0.01 wt. % of the dissolved solids contents.

Embodiment J9 is the concentrated glucaric acid product of any one of embodiments J1 to J8 wherein the $C_2$-$C_5$ di-acids are xylaric acid, tartaric acid, tartronic acid, and oxalic acid.

When introducing elements of the present invention or the preferred embodiments(s) thereof, the articles "a", "an", "the" and "said" are intended to mean that there are one or more of the elements. The terms "comprising", "including" and "having" are intended to be inclusive or open-ended and mean that there may be additional elements other than the listed elements and do not exclude unrecited elements or steps.

In view of the above, it will be seen that the several objects of the invention are achieved and other advantageous results attained.

As various changes could be made in the above products and processes without departing from the scope of the invention, it is intended that all matter contained in the above description shall be interpreted as illustrative and not in a limiting sense.

What is claimed is:

1. A product comprising an aqueous extract and a separation media comprising a resin in contact with the aqueous extract, the aqueous extract comprising:
   from about 85 wt. % to about 99 wt. % glucaric acid and any lactones thereof,
   gluconic acid and any lactones thereof, wherein the concentration of the gluconic acid and any lactones thereof is less than about 5 wt. %,
   from about 0.1 wt. % to about 5 wt. % guluronic acid and any lactones thereof,
   less than about 2.5 wt. % of one or more ketogluconic acids and any lactones thereof,
   less than about 10 wt. % of one or more $C_2$-$C_5$ di-acids and any lactones thereof, and
   less than about 1 wt. % glucose, wherein each weight percent is based on the dissolved solids content of the product.

2. The product of claim 1 comprising from about 0.1 wt. % to about 2.5 wt. % guluronic acid and any lactones thereof based on the dissolved solids content.

3. A product comprising an aqueous extract and a separation media comprising a resin in contact with the aqueous extract, the aqueous extract comprising:
   from about 85 wt. % to about 99 wt. % glucaric acid and any lactones thereof,
   from about 1 wt. % to about 5 wt. % gluconic acid and any lactones thereof,
   from about 0.1 wt. % to about 5 wt. % guluronic acid and any lactones thereof,
   less than about 2.5 wt. % of one or more ketogluconic acids and any lactones thereof,
   less than about 10 wt. % of one or more $C_2$-$C_5$ di-acids and any lactones thereof, and
   less than about 1 wt. % glucose, wherein each weight percent is based on the dissolved solids content of the product.

4. The product of claim 1 wherein the concentration of the ketogluconic acids and any lactones thereof is from about 0.01 wt. % to about 1 wt. % of the dissolved solids content and wherein the ketogluconic acids are a mixture of 2-ketogluconic acid, 3-ketogluconic acid, 4-ketogluconic acid, and 5-ketogluconic acid.

5. A product comprising an aqueous extract and a separation media comprising a resin in contact with the aqueous extract, the aqueous extract comprising:
   from about 85 wt. % to about 99 wt. % glucaric acid and any lactones thereof,
   gluconic acid and any lactones thereof, wherein the concentration of the gluconic acid and any lactones thereof is less than about 5 wt. %,
   from about 0.1 wt. % to about 5 wt. % guluronic acid and any lactones thereof,
   less than about 2.5 wt. % of one or more ketogluconic acids and any lactones thereof,
   from about 1 wt. % to about 10 wt. % $C_2$-$C_5$ di-acids and any lactones thereof, and
   less than about 1 wt. % glucose, wherein each weight percent is based on the dissolved solids content of the product.

6. The product of claim 1 wherein the $C_2$-$C_5$ di-acids comprise tartaric acid, tartronic acid, and oxalic acid.

7. The product of claim 1 wherein the product contains less than about 0.01 wt. % of nitric acid and salts thereof.

8. The product of claim 1 wherein the product is free of nitric acid and salts thereof.

9. The product of claim 1 wherein the concentration of glucaric acid and any lactones thereof is from about 90 wt. % to about 95 wt. % of the dissolved solids content.

10. The product of claim 4 wherein the concentration of glucaric acid and any lactones thereof is from about 90 wt. % to about 95 wt. % of the dissolved solids content.

11. The product of claim 1 wherein the concentration of gluconic acid and any lactones thereof is from about 1 wt. % to about 2.5 wt. % of the dissolved solids content.

12. The product of claim 9 wherein the concentration of the $C_2$-$C_5$ di-acids and any lactones thereof is from about 2.5 wt. % to about 7.5 wt. % of the dissolved solids content.

13. The product of claim 12 wherein the $C_2$-$C_5$ di-acids comprise tartaric acid, tartronic acid, and oxalic acid.

14. The product of claim 1 wherein the glucose concentration is less than about 0.1 wt. % of the dissolved solids content.

15. The product of claim 1 wherein the ketogluconic acids are a mixture of 2-ketogluconic acid, 3-ketogluconic acid, 4-ketogluconic acid, and 5-ketogluconic acid.

16. The product of claim 10 wherein the concentration of the one or more $C_2$-$C_5$ di-acids and any lactones thereof is from about 2.5 wt. % to about 7.5 wt. % of the dissolved solids content.

17. The product of claim 16 wherein the $C_2$-$C_5$ di-acids comprise tartaric acid, tartronic acid, and oxalic acid.

18. The product of claim 17 wherein the concentration of guluronic acid and any lactones thereof is from about 0.1 wt. % to about 2.5 wt. % based on the dissolved solids content.

19. The product of claim 5 wherein the concentration of glucaric acid and any lactones thereof is from about 90 wt. % to about 95 wt. % of the dissolved solids content.

20. The product of claim 1 wherein the resin comprises an anion exchange chromatography resin.

21. The product of claim 20 wherein the anion exchange chromatography resin is in glucarate form.

22. The product of claim 20 wherein the anion exchange chromatography resin comprises a weakly basic anion exchange chromatography resin.

23. The product of claim 20 wherein the anion exchange chromatography resin comprises from about 60% to about 100% weak base functionality.

24. The product of claim 20 wherein the anion exchange chromatography resin comprises from about 0% to about 40% strong base functionality.

* * * * *